United States Patent
Chen et al.

(10) Patent No.: US 12,367,579 B2
(45) Date of Patent: Jul. 22, 2025

(54) SYSTEMS AND METHODS TO PROCESS ELECTRONIC MEDICAL IMAGES FOR DIAGNOSTIC OR INTERVENTIONAL USE

(71) Applicant: Anode IP LLC, Tampa, FL (US)

(72) Inventors: John Chen, Tampa, FL (US); Craig Chappell, Provo, UT (US); Samuel Chang, Austin, TX (US)

(73) Assignee: Anode IP LLC, Tampa, FL (US)

( * ) Notice: Subject to any disclaimer, the term of this patent is extended or adjusted under 35 U.S.C. 154(b) by 0 days.

(21) Appl. No.: 18/490,906

(22) Filed: Oct. 20, 2023

(65) Prior Publication Data
US 2024/0104733 A1    Mar. 28, 2024

Related U.S. Application Data

(63) Continuation of application No. 17/657,643, filed on Apr. 1, 2022, now Pat. No. 11,830,189.
(Continued)

(51) Int. Cl.
*G06T 7/00* (2017.01)
*A61B 8/00* (2006.01)
*G06N 20/20* (2019.01)

(52) U.S. Cl.
CPC ............ *G06T 7/0012* (2013.01); *A61B 8/461* (2013.01); *A61B 8/5215* (2013.01);
(Continued)

(58) Field of Classification Search
CPC ..... A61B 8/461; A61B 8/5215; A61B 8/5292; G06N 20/20; G06T 2207/10132;
(Continued)

(56) References Cited

U.S. PATENT DOCUMENTS

2004/0242987 A1* 12/2004 Liew .................. A61B 8/5223
600/407
2012/0172700 A1* 7/2012 Krishnan ............... A61B 6/505
600/407
(Continued)

OTHER PUBLICATIONS

Josefina Gutierrez-Martinez et al., "Computer-aided diagnosis in rheumatic diseases using ultrasound: an overview," Nov. 6, 2019, Clinical Rheumatology, 39, pp. 993-1005 (Year: 2019).*
(Continued)

*Primary Examiner* — Chao Sheng
*Assistant Examiner* — Maria Christina Talty
(74) *Attorney, Agent, or Firm* — Bookoff McAndrews, PLLC

(57) ABSTRACT

Systems and methods are disclosed herein for processing ultrasound images to identify objects for diagnostic and/or interventional use. For instance, an ultrasound image of an anatomical structure may be received from a computing device of an ultrasound imaging system. The ultrasound image may be input to a machine learning model that is trained to identify a plurality of objects in ultrasound images of the anatomical structure. The plurality of objects may include anatomical features, disruptive features, and/or instruments. A prediction of one or more objects from the plurality of objects identified in the ultrasound image may be received as output of the machine learning model. An indication of the prediction may be provided to the computing device for display on a display of the ultrasound imaging system.

20 Claims, 16 Drawing Sheets

Related U.S. Application Data

(60) Provisional application No. 63/170,377, filed on Apr. 2, 2021.

(52) U.S. Cl.
CPC .......... *A61B 8/5292* (2013.01); *G06N 20/20* (2019.01); *G06T 2207/10132* (2013.01)

(58) Field of Classification Search
CPC ...... G06T 7/0012; G16H 15/00; G16H 30/40; G16H 50/20; G16H 50/70
See application file for complete search history.

(56) References Cited

U.S. PATENT DOCUMENTS

| | | | | |
|---|---|---|---|---|
| 2016/0374644 | A1* | 12/2016 | Mauldin, Jr. | A61B 8/085 600/424 |
| 2018/0158209 | A1* | 6/2018 | Fine | G16H 30/40 |
| 2019/0340753 | A1 | 11/2019 | Brestel et al. | |
| 2020/0225811 | A1 | 7/2020 | Sieniek | |
| 2020/0297318 | A1 | 9/2020 | Naidu et al. | |
| 2020/0349308 | A1 | 11/2020 | Dayal et al. | |
| 2020/0402226 | A1* | 12/2020 | Peng | G06N 20/00 |
| 2021/0000449 | A1* | 1/2021 | Deo | A61B 5/7267 |
| 2021/0042564 | A1* | 2/2021 | Xiao | G16H 50/70 |
| 2021/0056690 | A1* | 2/2021 | Futamura | G06T 7/0012 |
| 2021/0077061 | A1 | 3/2021 | Pinkovich et al. | |
| 2022/0000448 | A1* | 1/2022 | Starns | A61B 8/4455 |

OTHER PUBLICATIONS

YiRang Shin et al., "Artificial intelligence in musculoskeletal ultrasound imaging," Sep. 6, 2020, Ultrasonography, 40, pp. 30-44 (Year: 2020).*

Brady, A.P., Error and discrepancy in radiology: inevitable or avoidable?, Insights Imaging, Feb. 2017, 8(1):171-182, https://www.ncbi.nlm.nih.gov/pmc/articles/PMC5265198/ [retrieved on Mar. 31, 2022]. Retrieved from the Internet (12 pages).

Jacobson, J. A. Fundamentals of Musculoskeletal Ultrasound, 2018, pp. 2-9, 16, 407-442. Elsevier, Inc., USA.

Kim, Y.W. and Mandfield, L.T., Fool Me Twice: Delayed Diagnoses in Radiology With Emphasis on Perpetuated Errors, AJR, Mar. 2014, 202(3): 465-470, https://www.ajronline.org/doi/10.2214/AJR.13.11493 [retrieved on Mar. 31, 2022]. Retrieved from the Internet (6 pages).

Pixel Perfect Automated Image Labeling, V7Labs, no date but published before Mar. 31, 2022, https://www.v7labs.com/annotation [retrieved on Mar. 31, 2022]. Retrieved from the Internet (8 pages).

Report to the Congress: Medicare and the Health Care Delivery System, MedPAC, Jun. 14, 2019, pp. 3-454, https://www.medpac.gov/document/http-www-medpac-gov-docs-default-source-reports-jun19_medpac_reporttocongress_sec-pdf/ [retrieved on Mar. 31, 2022]. Retrieved from the Internet (420 pages).

Sunshine, J.H., Radiology Practice in the United States: Overview from the American College of Radiology, Dec. 1, 2008, 8(5): 1-3, https://healthmanagement.org/c/imgfr/issuearticle/radiology-practice-in-the-united-states-overview-from-the-american-college-of-radiology [retrieved on Mar. 31, 2022]. Retrieved from the Internet (3 pages).

Top 10 Issues Limiting Deployment of AI Tools, 2019 Annual Report of the Data Science Institute of the American College of Radiology, 2019, p. 7, https://www.acrdsi.org/-/media/DSI/Files/PDFs/DSI-Annual-Report_Final_Encrypted.pdf [retrieved on Mar. 31, 2022]. Retrieved from the Internet (1 page).

Topol, E.J., High-performance medicine: the convergence of human and artificial intelligence, Nature Medicine, Jan. 2109, 25:44-56, https://www.nature.com/articles/s41591-018-0300-7 [retrieved on Mar. 31, 2022]. Retrieved from the Internet (13 pages).

* cited by examiner

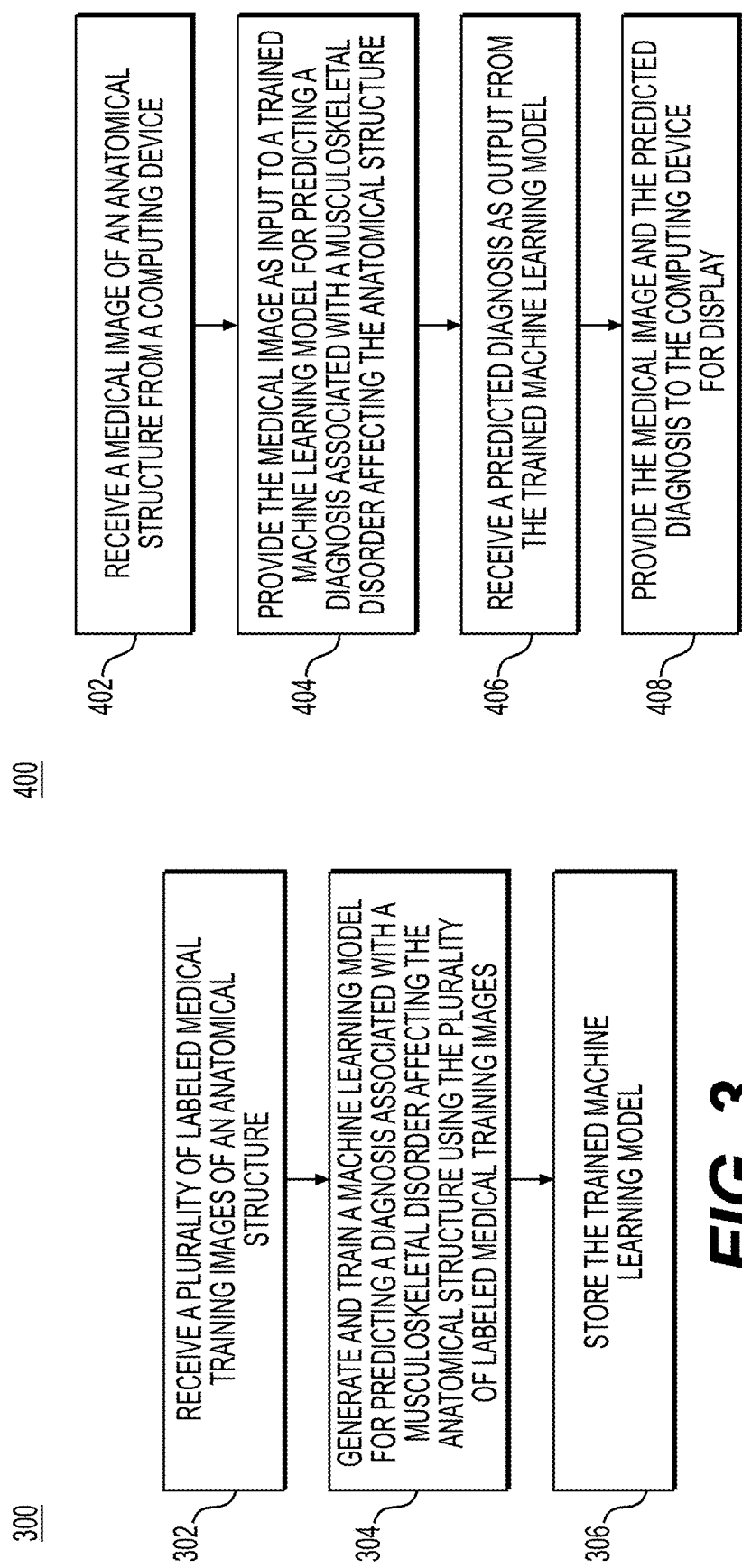

IMAGE FILENAME: IMAGE THREE.jpg
554 — PREDICTED CLASS: 4 FULL THICKNESS TEAR
556 — PREDICTION PROBABILITY: 77.81 %

```
558
   +------------------------------------------------------------+
   | IMAGE THREE.jpg SUPRASPINATUS CLASSIFICATION PROBABILITIES |
                                                                  562
560 -+-CLASS                            |           PROBABILITY (%)
   +----------------------------------+-------------------------+
   | 4 FULL THICKNESS TEAR            |                  77.81  |
   | 1 ARTICULAR SIDED TEAR           |                  19.21  |
   | 3 BURSAL SIDED TEAR              |                   2.23  |
   | 2 INTRASUBSTANCE TEAR            |                   0.73  |
   | 0 NORMAL                         |                   0.02  |
   +----------------------------------+-------------------------+
```

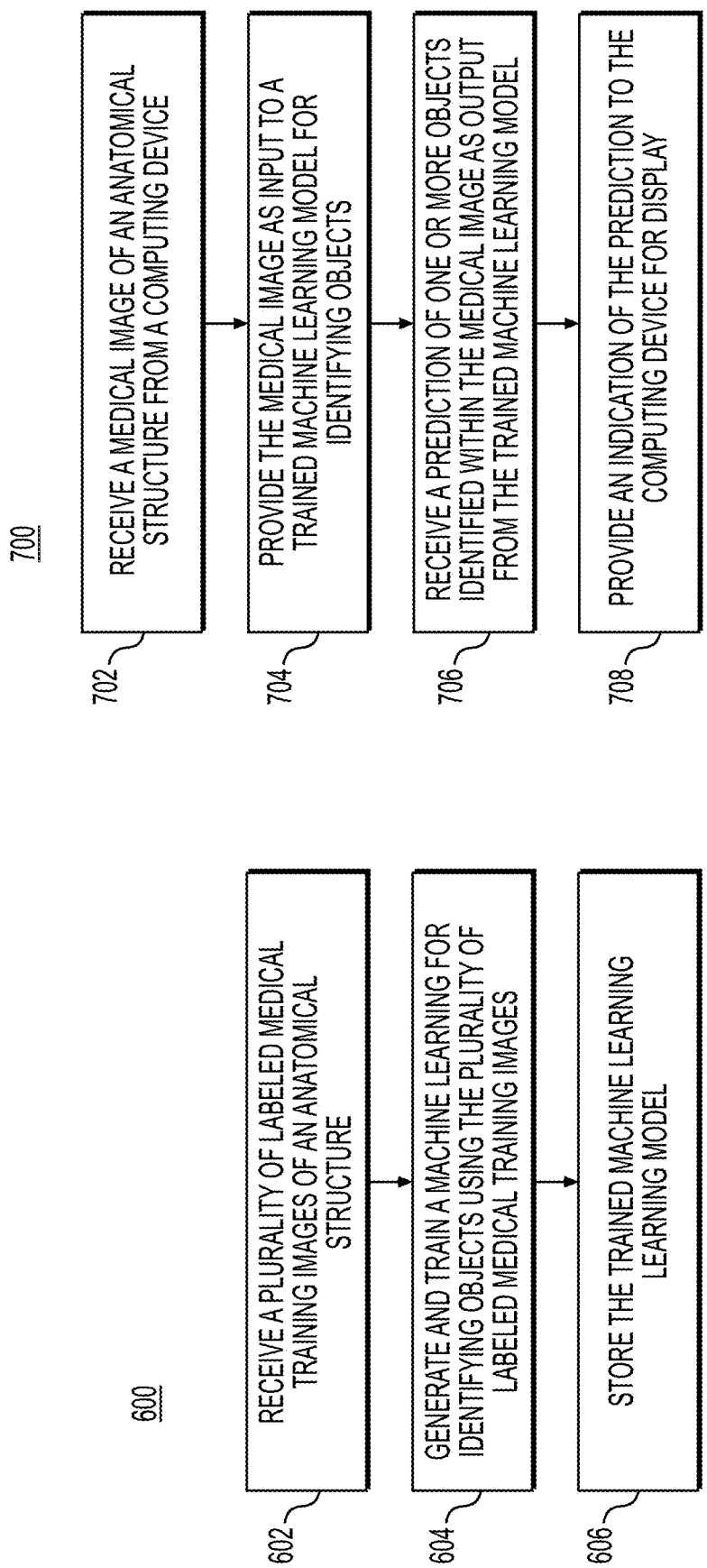

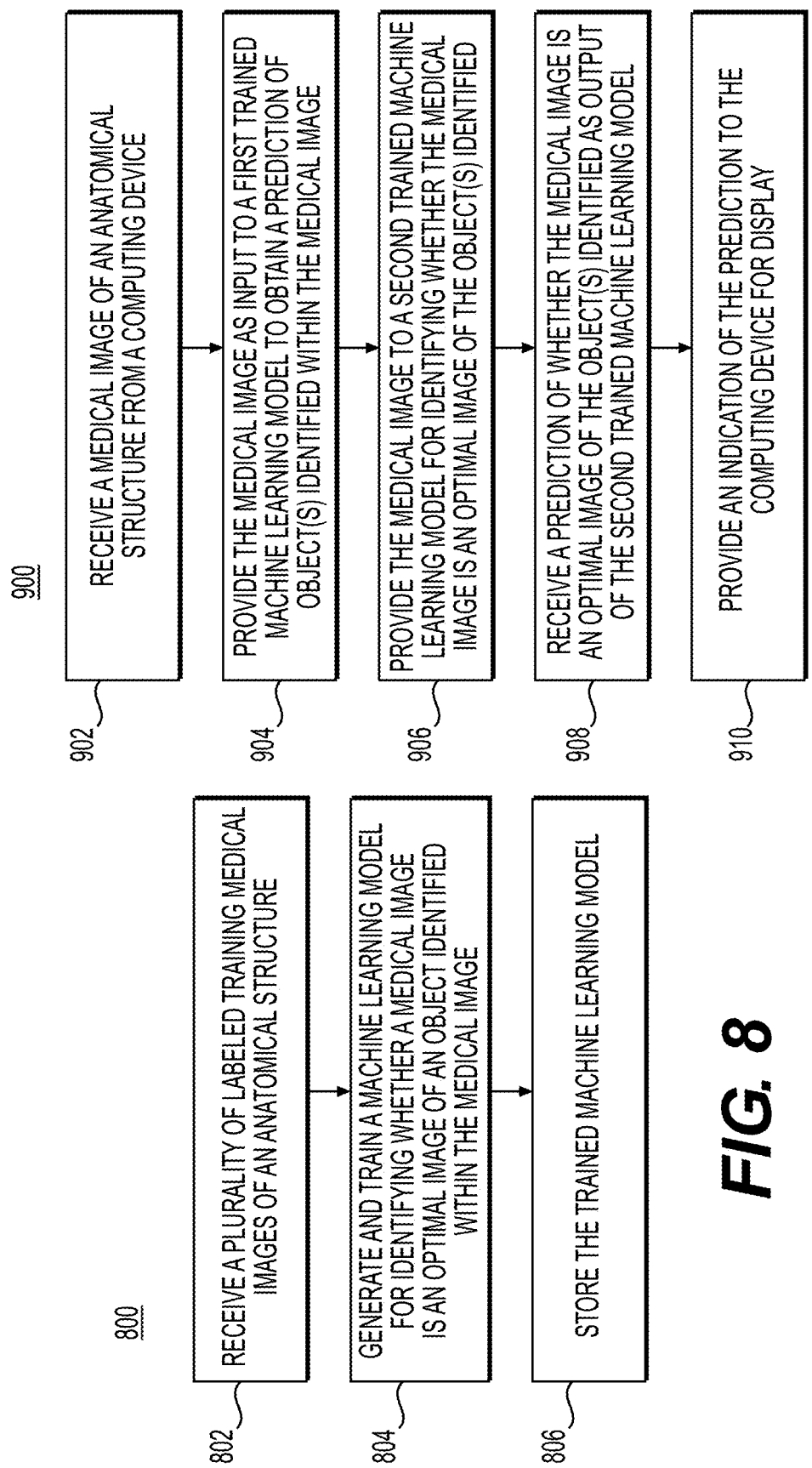

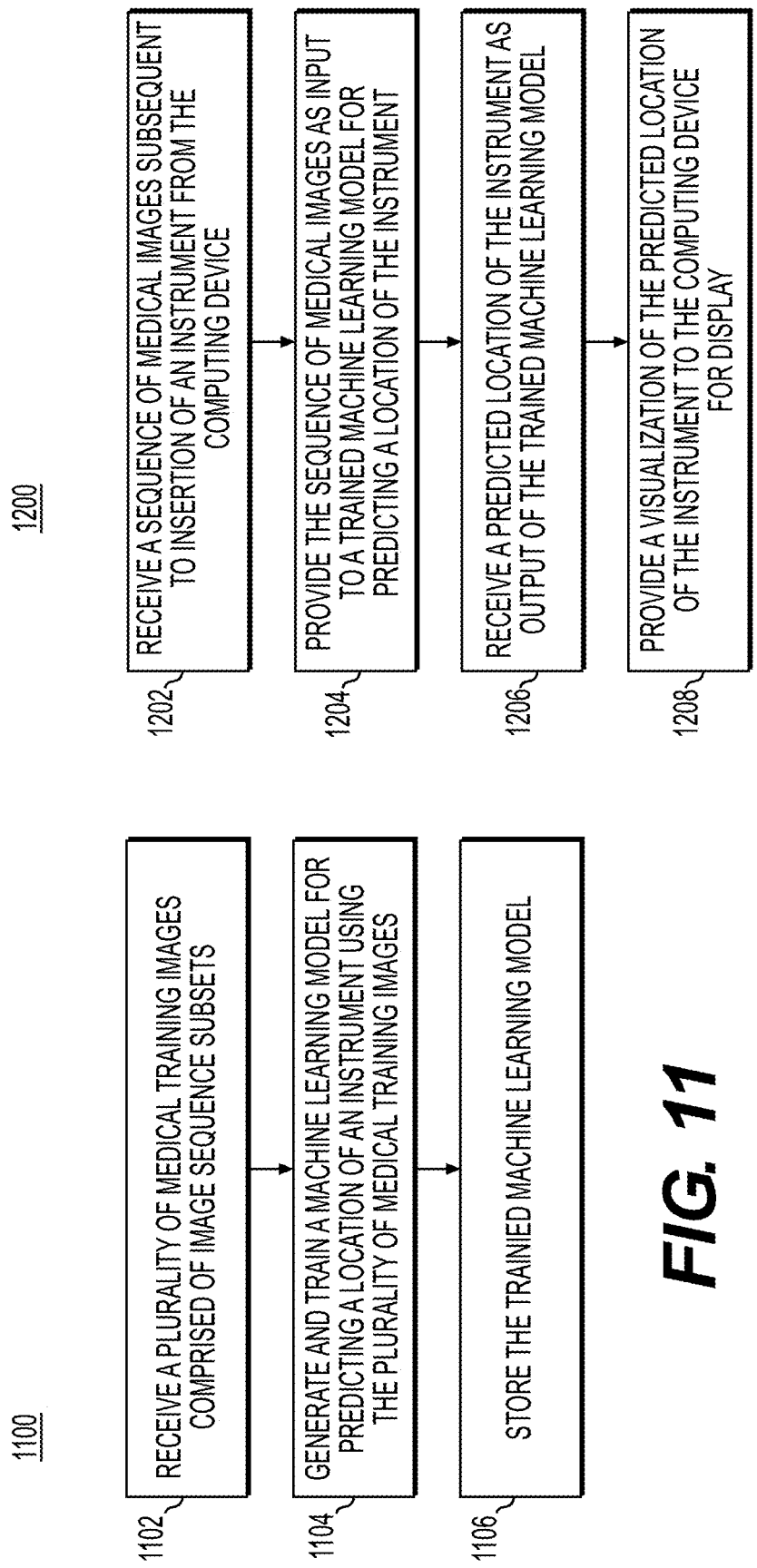

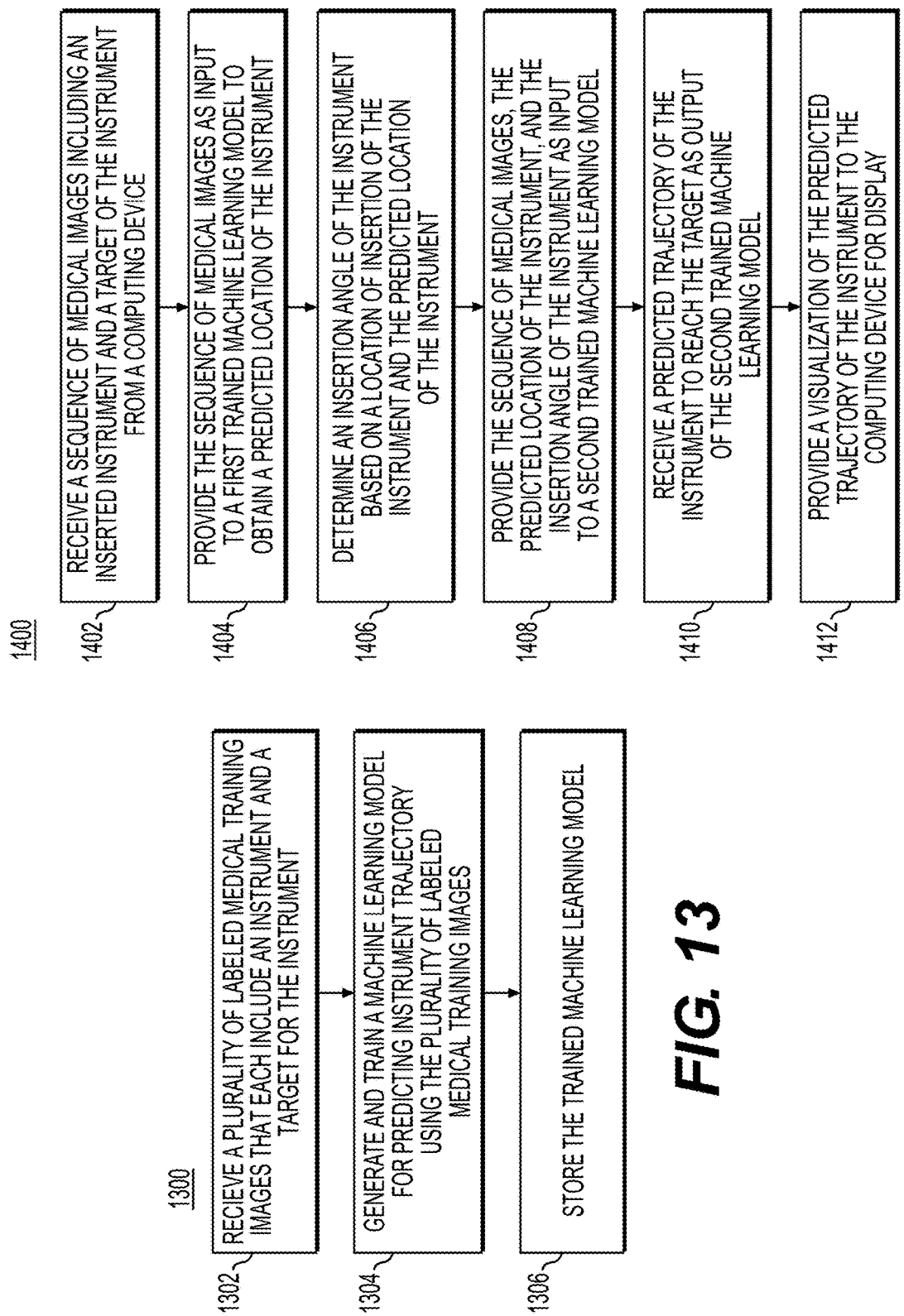

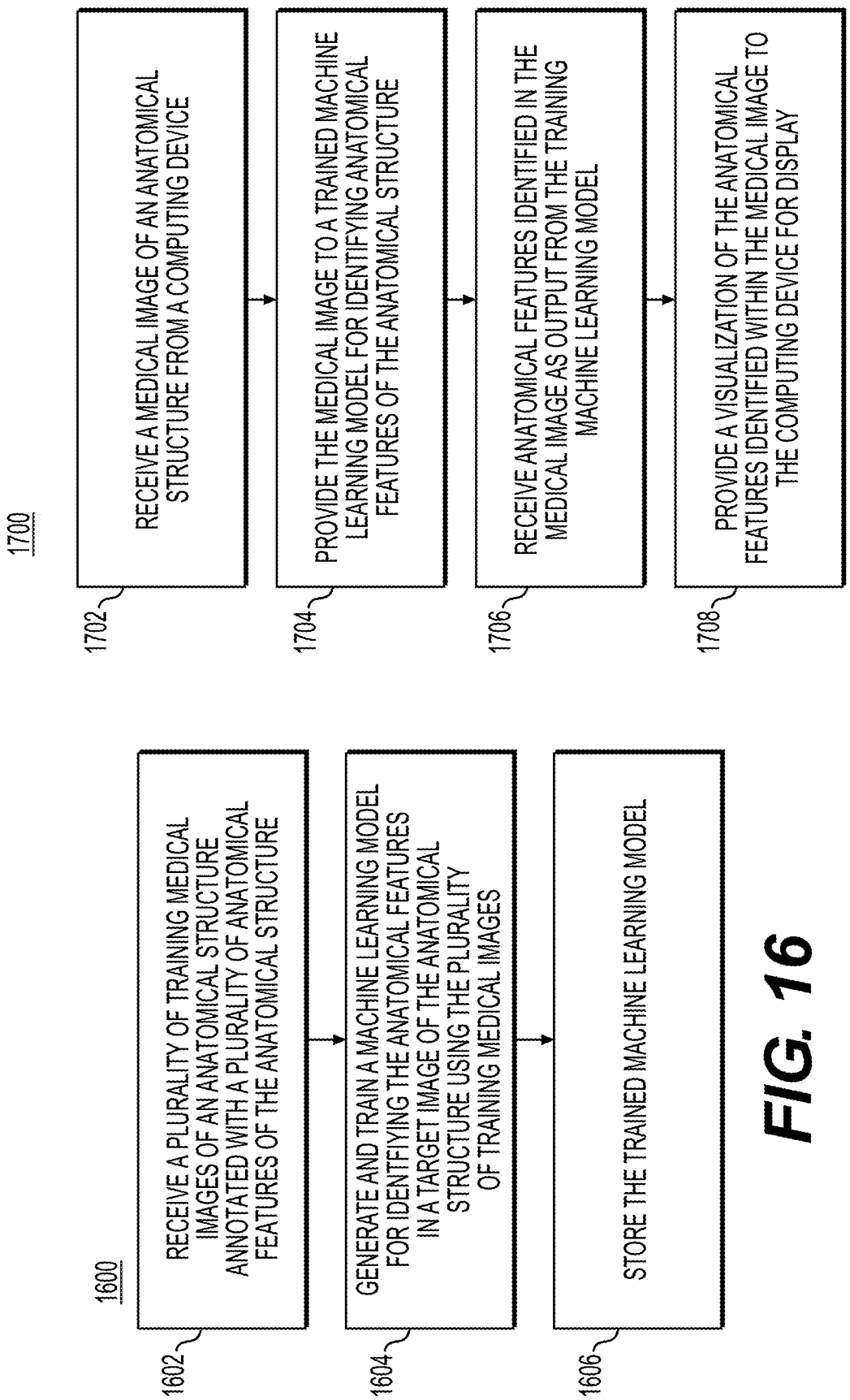

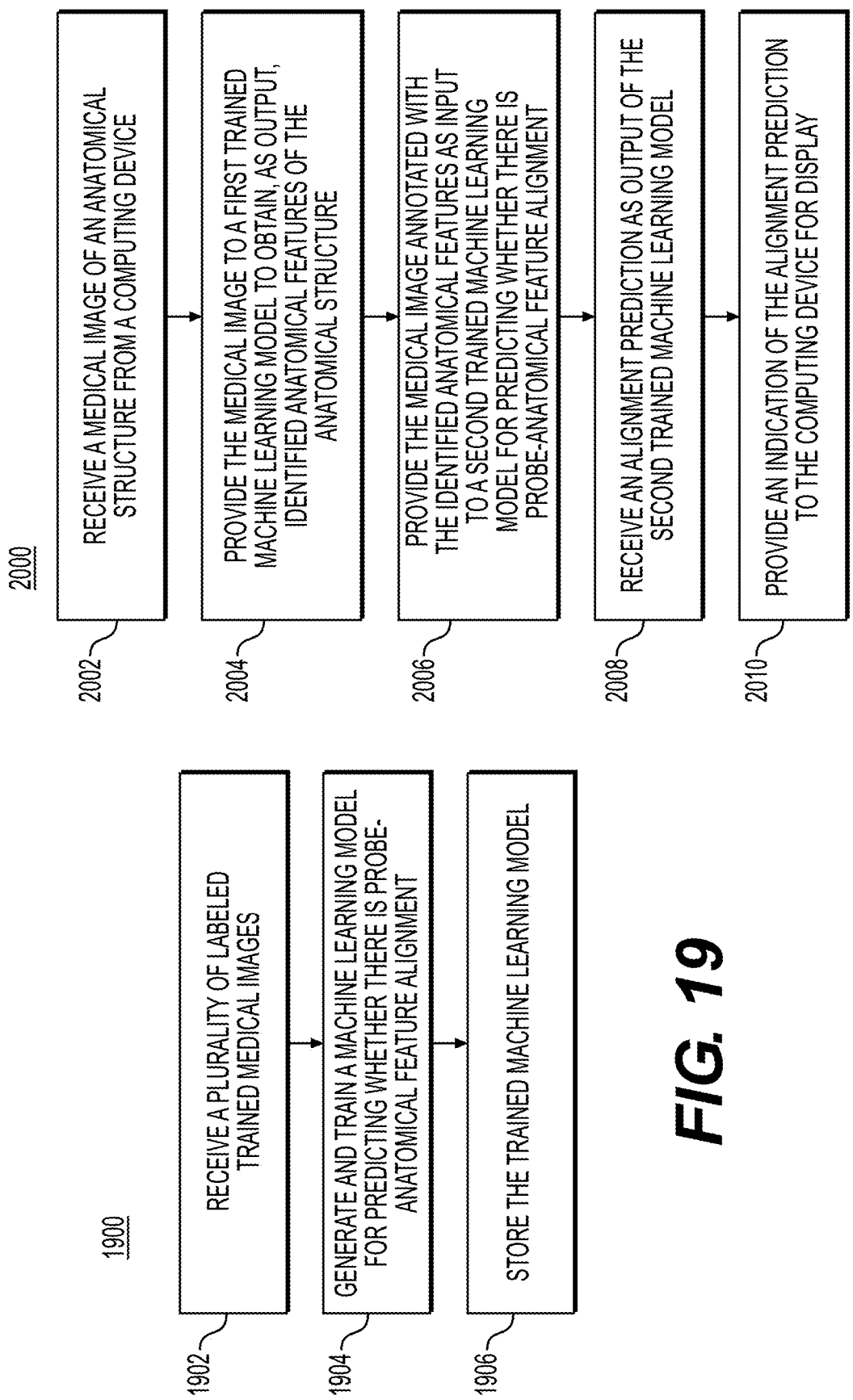

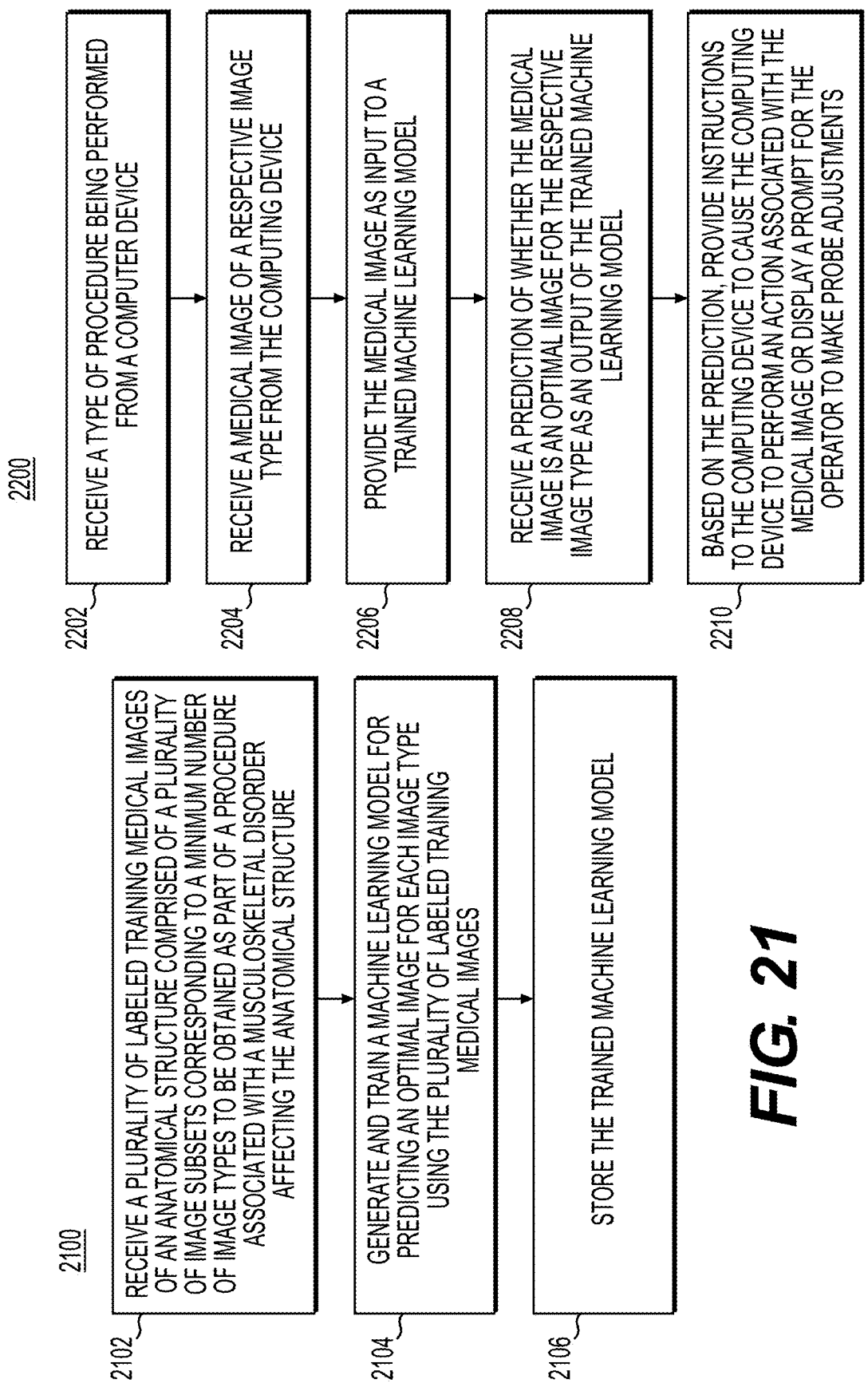

SYSTEMS AND METHODS TO PROCESS ELECTRONIC MEDICAL IMAGES FOR DIAGNOSTIC OR INTERVENTIONAL USE

CROSS-REFERENCE TO RELATED APPLICATION(S)

This patent application is a continuation of and claims the benefit of priority to U.S. Nonprovisional application Ser. No. 17/657,643, filed on Apr. 1, 2022, which claims priority to U.S. Provisional Application No. 63/170,377, filed on Apr. 2, 2021, the entireties of which are incorporated herein by reference.

FIELD OF THE DISCLOSURE

Various techniques presented herein pertain generally to processing electronic medical images for providing clinical diagnoses, measurements, and/or observations using artificial intelligence (AI). More specifically, particular techniques of the present disclosure relate to systems and methods for training and using machine learning models to predict clinical diagnoses, measurements, and/or observations associated with musculoskeletal disorders from diagnostic or interventional ultrasound images.

BACKGROUND

Musculoskeletal disorders significantly impact quality of life both in the US and globally. Imaging of anatomical structures affected by the musculoskeletal disorders may be used to facilitate clinical diagnoses of the disorders and/or as part of (e.g., to guide) interventions to treat the disorders. However, patients are becoming more concerned with overuse and/or misuse of expensive advanced medical imaging, such as computer tomography (CT), magnetic resonance imaging (MRI) and positron emission tomography (PET), that expose patients to scheduling delays, additional costs, and unnecessary radiation exposure. Therefore, alternative imaging techniques, such as ultrasound, may be increasingly used for diagnostic and intervention imaging associated with musculoskeletal disorders.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images, such as ultrasound images to identify objects for diagnostic and/or interventional use.

In one example aspect, systems are described for processing ultrasound images to identify objects. An example system may include a processor and a memory coupled to the processor. The memory may store instructions that, when executed by the processor, cause the system to perform operations. The operations may include receiving an ultrasound image of an anatomical structure from a computing device of an ultrasound imaging system, and providing the ultrasound image as input to a machine learning model that is trained to identify a plurality of objects in ultrasound images of the anatomical structure. The plurality of objects may include anatomical features, disruptive features, and/or instruments. The operations may further include receiving a prediction of one or more objects from the plurality of objects identified in the ultrasound image as output of the machine learning model, and providing an indication of the prediction to the computing device for display on a display of the ultrasound imaging system.

In another example aspect, methods are described for processing ultrasound images to identify objects. An example method may include receiving an ultrasound image of an anatomical structure from a computing device of an ultrasound imaging system, and providing the ultrasound image as input to a machine learning model that is trained to identify a plurality of objects in ultrasound images of the anatomical structure. The plurality of objects may include anatomical features, disruptive features, and/or instruments. The method may further include receiving a prediction of one or more objects from the plurality of objects identified in the ultrasound image as output of the machine learning model, and providing an indication of the prediction to the computing device for display on a display of the ultrasound imaging system.

In a further example aspect, non-transitory computer-readable media are described for processing ultrasound images to identify objects. An example non-transitory computer-readable medium may store instructions that, when executed by a processor, cause the processor to perform operations for processing ultrasound images to identify objects. The operations may include receiving an ultrasound image of an anatomical structure from a computing device of an ultrasound imaging system, and providing the ultrasound image as input to a machine learning model that is trained to identify a plurality of objects in ultrasound images of the anatomical structure. The plurality of objects may include anatomical features, disruptive features, and/or instruments. The operations may further include receiving a prediction of one or more objects from the plurality of objects identified in the ultrasound image as output of the machine learning model, and providing an indication of the prediction to the computing device for display on a display of the ultrasound imaging system.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated into and constitute a part of this specification, illustrate various exemplary embodiments and together with the description, serve to explain the principles of the disclosed embodiments.

FIG. 3 depicts a flowchart illustrating an exemplary method for training a machine learning model to predict a diagnosis of a musculoskeletal disorder, according to techniques described herein.

FIG. 4 depicts a flowchart illustrating an exemplary method for predicting a diagnosis of a musculoskeletal disorder, according to techniques described herein.

FIG. 6 depicts a flowchart illustrating an exemplary method for training a machine learning model to identify objects within a medical image of an anatomical structure, according to techniques described herein.

FIG. 7 depicts a flowchart illustrating an exemplary method for identifying objects within a medical image of an anatomical structure, according to techniques described herein.

FIG. 8 depicts a flowchart illustrating an exemplary method for training a machine learning model to identify an optimal image of an object identified within a medical image of an anatomical structure, according to techniques described herein.

FIG. 9 depicts a flowchart illustrating an exemplary method for determining whether a medical image is an optimal image of an objected identified therein, according to techniques described herein.

FIG. 11 depicts a flowchart illustrating an exemplary method for training a machine learning model to predict a location of an instrument, according to techniques described herein.

FIG. 12 depicts a flowchart illustrating an exemplary method for predicting a location of an instrument, according to techniques described herein.

FIG. 13 depicts a flowchart illustrating an exemplary method for training a machine learning model to predict instrument trajectory, according to techniques described herein.

FIG. 14 depicts a flowchart illustrating an exemplary method for predicting instrument trajectory, according to techniques described herein.

FIG. 16 depicts a flowchart illustrating an exemplary method for training a machine learning model to identify anatomical features, according to techniques described herein.

FIG. 17 depicts a flowchart illustrating an exemplary method for visualizing anatomical features of an anatomical structure identified in a medical image, according to techniques described herein.

FIG. 19 depicts a flowchart illustrating an exemplary method for training a machine learning model to detect probe alignment with an anatomical feature identified within a medical image, according to techniques described herein.

FIG. 20 depicts a flowchart illustrating an exemplary method for detecting probe alignment with one or more anatomical features of an anatomical structure identified within a medical image of the anatomical structure, according to techniques described herein.

FIG. 21 depicts a flowchart illustrating an exemplary method for training a machine learning model to identify an optimal image frame, according to techniques described herein.

FIG. 22 depicts a flowchart illustrating an exemplary method for capturing an optimal image frame, according to techniques described herein.

DETAILED DESCRIPTION OF THE EMBODIMENTS

Figure 1:
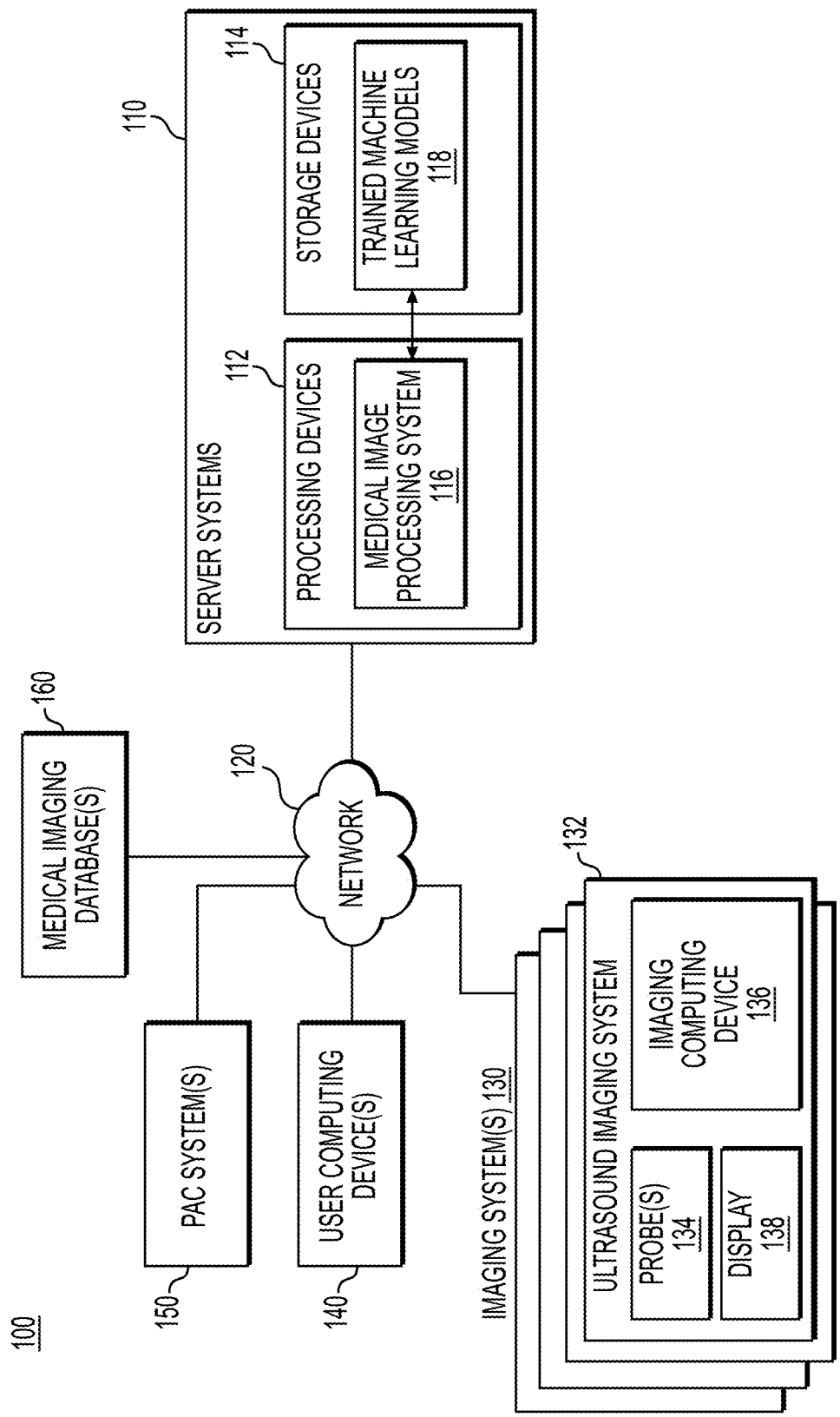
FIG. 1 illustrates an exemplary block diagram of a network environment for processing electronic medical images, according to techniques described herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

In diagnostic imaging, a physician may evaluate electronic images during an imaging exam of a patient to facilitate diagnoses of disorders, injuries, and/or conditions, including any classifications thereof (e.g., categories, stages, phases, grades, etc.). In interventional imaging, a physician may utilize electronic images during a procedure to e.g., visualize instruments inserted into the patient's body to assist the physician in safely guiding the instruments to an intended target area. Conventionally, advanced medical imaging, such as computer tomography (CT), magnetic resonance imaging (MRI) and positon emission tomography (PET), has been used for diagnostic and/or interventional imaging. However, alternative imaging techniques, such as ultrasound, may also be used for diagnostic and intervention imaging, and particularly for musculoskeletal disorders. Due to lower costs, ultrasound imaging systems are more readily available (e.g., a physician may have access to multiple ultrasound systems but only one CT imaging system) which reduces scheduling delays and passes on lower costs to the patients. Additionally, ultrasound imaging avoids exposing the patient to radiation. Ultrasound devices may also be portable, allowing for mailing the device to remote locations, or otherwise allowing for quicker transportation or access in remote or difficult geographic areas.

Techniques disclosed herein provide AI tools for diagnostic and/or interventional ultrasound imaging. For example, a plurality of machine learning models may be trained and deployed to predict diagnoses, observations, and/or measurements associated with musculoskeletal disorders from ultrasound images. Example observations may include identification of objects within the ultrasound images such as anatomical features, features that are not normally present in the anatomical structure that may disrupt the body's function, and/or foreign bodies (e.g., instruments) inserted in the body. The observations may also include location and/or trajectory predictions of the objects, and/or predictions of whether an optimal image of the object is being captured. Visualizations based on the predictions may be generated and provided to the physicians in real-time as they are performing diagnostic examinations on patients and/or as they are performing an ultrasound-guided procedure, which may be to treat a diagnosed disorder.

While specific examples included throughout the present disclosure involve ultrasound imaging, it should be understood that techniques according to this disclosure may be adapted to other types of imaging modalities. For example, the techniques may be adapted to any medical imaging modality, such as MRI, CT, PET, X-ray or the like.

The Environment

FIG. 1 illustrates an exemplary block diagram of an environment 100 for processing electronic medical images, according to an exemplary technique of the present disclosure. The environment may include server systems 110 that communicate, over a network 120, within one or more imaging systems 130, one or more user computing devices 140, one or more picture archiving and communication (PAC) systems 150, and/or medical imaging databases 160.

The server systems 110 may include processing devices 112 and storage devices 114. The processing devices 112 may be configured to implement a medical image processing system 116, hereinafter system 116. The system 116 may apply AI, machine learning, and/or image processing techniques to medical images that are received, e.g., from the imaging systems 130, user computing devices 140, or PAC systems 150 over the network 120. Alternatively, the system 116, trained machine learning models 118, or other features described with server systems 110 may be located with the imaging system 130 itself. Further, techniques discussed herein as being performed by the system 116 may be performed by the imaging computing device 136 or user computing device 140, for example.

For example, the system 116 may include a training image platform configured to generate and train a plurality of trained machine learning models 118 based on datasets of training medical images received, e.g., from one or more medical imaging databases 160 over the network 120. The training medical images may be images of anatomical structures of humans and/or animal (e.g., in veterinary context). The training medical images may be real images or synthetically generated images to compensate for data sparsity, if needed. The training medical images received may be annotated by physicians and/or other healthcare professionals. For a given training medical image of an anatomical structure, the following may be annotated: anatomical features of the anatomical structure, features that are not normally present in the anatomical structure that may disrupt the body's function, foreign bodies, measurements associated with the features and/or the bodies, a diagnosis identifiable from the image, and/or an image view type (e.g., a probe orientation), as described in detail elsewhere herein. The training medical images may be annotated using one or more of the known or future data annotation techniques, such as polygons, brushes/erasers, bounding boxes, keypoints, keypoint skeletons, lines, ellipses, cuboids, classification tags, attributes, instance/object tracking identifiers, free text, and/or directional vectors, in order to train any one or more of the known or future model types, such as image classifiers, video classifiers, image segmentation, object detection, object direction, instance segmentation, semantic segmentation, volumetric segmentation, composite objects, keypoint detection, keypoint mapping, 2-Dimension/3-Dimension and 6 degrees-of-freedom object poses, pose estimation, regressor networks, ellipsoid regression, 3D cuboid estimation, optical character recognition, text detection, and/or artifact detection.

The trained machine learning models 118 may include convolutional neural networks (CNNs), support vector machines (SVMs), generative adversarial networks (GANs), and/or other similar types of models that are trained using supervised, unsupervised, and/or reinforcement learning techniques. For example, as used herein, a "machine learning model" generally encompasses instructions, data, and/or a model configured to receive input, and apply one or more of a weight, bias, classification, or analysis on the input to generate an output. The output may include, e.g., a classification of the input, an analysis based on the input, a design, process, prediction, or recommendation associated with the input, or any other suitable type of output. A machine learning system or model may be trained using training data, e.g., experiential data and/or samples of input data, which are fed into the system in order to establish, tune, or modify one or more aspects of the system, e.g., the weights, biases, criteria for forming classifications or clusters, or the like. The training data may be generated, received, and/or otherwise obtained from internal or external resources. Aspects of a machine learning system may operate on an input linearly, in parallel, via a network (e.g., a neural network), or via any suitable configuration.

The execution of the machine learning system may include deployment of one or more machine learning techniques, such as linear regression, logistical regression, random forest, gradient boosted machine (GBM), deep learning, and/or a deep neural network (e.g., multi-layer perceptron (MLP), CNN, recurrent neural network). Supervised and/or unsupervised training may be employed. For example, supervised learning may include providing training data and labels corresponding to the training data, e.g., as ground truth. Training data may comprise medical images annotated by human technicians and/or other healthcare professionals. Unsupervised approaches may include clustering, classification, or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc. Alternatively, reinforcement learning may be employed for training. For example, reinforcement learning may include training an agent interacting with an environment to make a decision based on the current state of the environment, receive feedback (e.g., a positive or negative reward based on accuracy of decision), adjusts its decision to maximize the reward, and repeat again until a loss function is optimized.

The trained machine learning models 118 may be stored by the storage device 114 to allow subsequent retrieval and use by the system 116, e.g., when a medical image is received for processing. In other techniques, a third party system may generate and train the plurality of trained machine learning models 118. The server systems 110 may receive the trained machine learning models 118 from the third party system and store within the storage devices 114.

The imaging systems 130 may include systems implementing a plurality of different imaging modalities. For example, one of the imaging systems 130 may be an ultrasound imaging system 132. The ultrasound imaging system 132 may include one or more probes 134 (e.g., transducer), an imaging computing device 136 communicatively coupled to the probe 134, and a display 138. Once placed in contact with a patient's skin (human or animal) near an anatomical structure to be imaged, the probe may emit sound waves into the patient's body and receive sound waves that are reflected back from which images may be created by the imaging computing device 136. For example, the probe 134 may generate electric signals based on the reflected sound waves that are transmitted to the imaging computing device 136 to generate the images. The images may then be presented on the display 138. A frequency and depth at which the sound waves are sent by the probe 134 may be adjustable settings of the ultrasound imaging system 132. The images may be live images. Controls of the ultrasound imaging system 132 may enable the live image to be frozen and captured as a still image. Other example imaging systems perform x-ray imaging, CT, MRI, and/or PET systems.

In some examples, the images generated by the imaging systems 130 may be transmitted over the network 120 to the user computing devices 140 for viewing by a physician. For example, after the patient is imaged using the ultrasound imaging system 132 (e.g., by a technician qualified to operate the ultrasound imaging system 132), the images generated may be transmitted to one or more of the user computing devices 140 (e.g., a computing device of physician) for initial analysis. The user computing devices 140 may include a desktop computer, a laptop computer, a tablet, a smart cellular phone (e.g., a mobile phone), a smart watch or other electronic wearable, etc. Additionally or alternatively, the images generated by the imaging systems 130 may be transmitted to one of the PAC systems 150 for storage over the network 120.

At least a portion of one or more instructions stored in a memory of the imaging computing device 136 of the ultrasound imaging system 132 and/or a memory of user computing device 140 may include instructions for executing an application associated with the system 116 (e.g., a client application) that is configured to communicate with the server systems 110 over the network 120. As one illustrative example, as a patient is being imaged using the ultrasound imaging system 132, the application may be executing on the imaging computing device 136 to enable real-time processing of images generated by the system 116. As another illustrative example, the application may be executing on the user computing device 140 and a user (e.g., the physician) may select previously captured and stored images (e.g. from the PAC system 150) for processing by the system 116. In some examples, the application may be able to capture (e.g., via a voice interface) and process voice commands from the physician.

Additionally, one or more components of the imaging computing device 136 and/or computing device 140 may generate, or may cause to be generated, one or more graphic user interfaces (GUIs) based on instructions/information stored in the memory, instructions/information received from the other systems in the environment 100, and/or the like and may cause the GUIs to be displayed via a display of the respective devices. The GUIs may be, e.g., mobile application interfaces or browser user interfaces and may include text, input text boxes, selection controls, and/or the like. The display may include a touch screen or a display with other input systems (e.g., a mouse, keyboard, etc.) for the managing contact and/or guest contact of the respective devices to control the functions thereof.

The network 120 over which the one or more components of the environment 100 communicate may include one or more wired and/or wireless networks, such as a wide area network ("WAN"), a local area network ("LAN"), personal area network ("PAN"), a cellular network (e.g., a 3G network, a 4G network, a 5G network, etc.) or the like. In one technique, the network 120 includes the Internet, and information and data provided between various systems occurs online. "Online" may mean connecting to or accessing source data or information from a location remote from other devices or networks coupled to the Internet. Alternatively, "online" may refer to connecting or accessing an electronic network (wired or wireless) via a mobile communications network or device. The server systems 110, imaging systems, computing device 140, PAC systems 150, and/or medical imaging databases 160 may be connected via the network 120, using one or more standard communication protocols.

Although depicted as separate components in FIG. 1, it should be understood that a component or portion of a component in the system of exemplary environment 100 may, in some embodiments, be integrated with or incorporated into one or more other components. For example, the display 138 may be integrated with the imaging computing device 136 of the ultrasound imaging system or the like. In some embodiments, operations or aspects of one or more of the components discussed above may be distributed amongst one or more other components. Any suitable arrangement and/or integration of the various systems and devices of the exemplary environment 100 may be used.

In the following disclosure, various acts may be described as performed or executed by a component from FIG. 1, such as the server systems 110, imaging systems, the computing device 140, or components thereof. However, it should be understood that in various embodiments, various components of the exemplary environment 100 discussed above may execute instructions or perform acts including the acts discussed below. An act performed by a device may be considered to be performed by a processor, actuator, or the like associated with that device. Further, it should be understood that in various embodiments, various steps may be added, omitted, and/or rearranged in any suitable manner.

High Level Overview of Medical Image Processing

Figure 2:
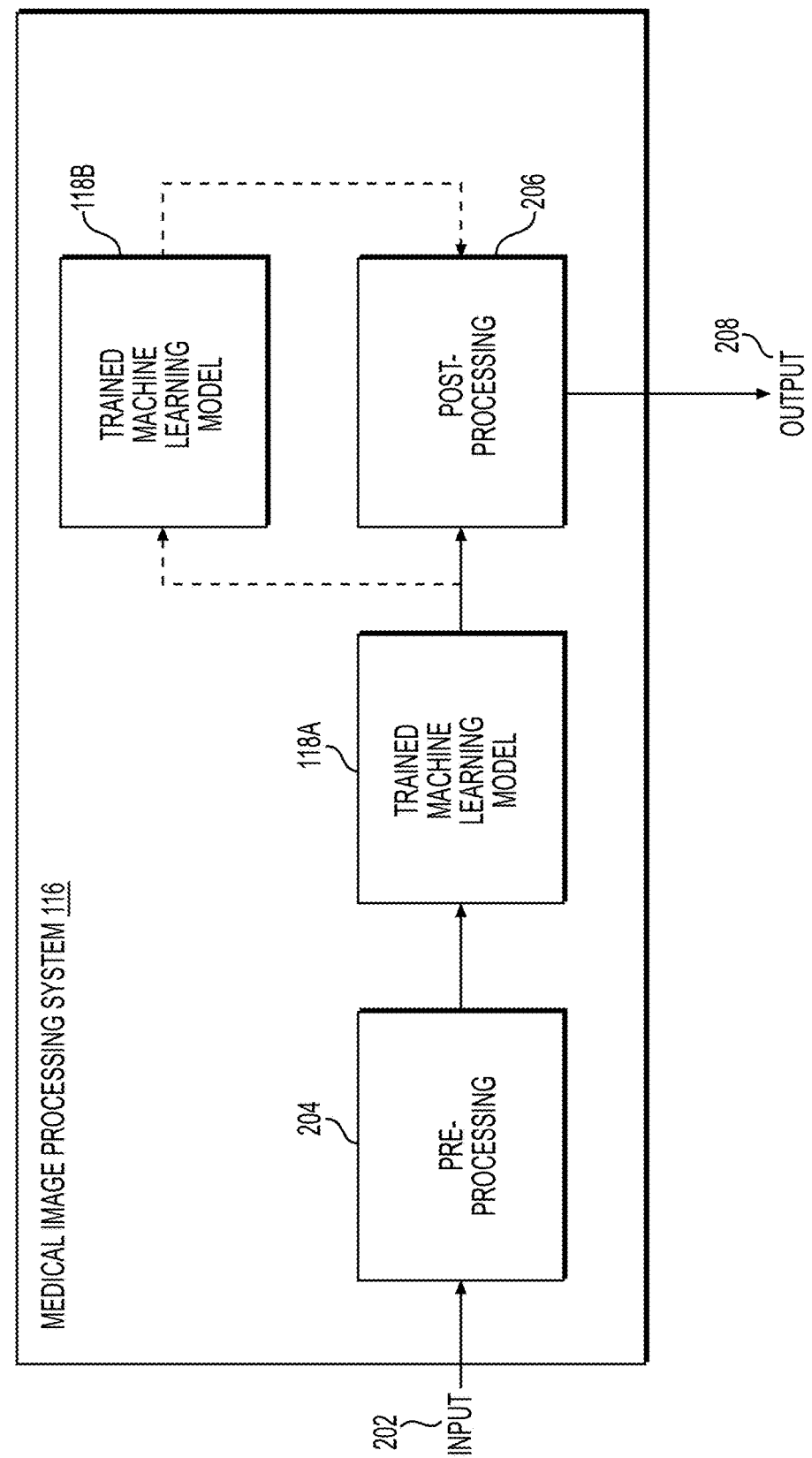
FIG. 2 depicts a block diagram of an exemplary process performed by a medical image processing system, according to techniques described herein.

FIG. 2 depicts a block diagram of an exemplary process 200 performed by the system 116. Process 200 may begin when input 202 is received at the system 116. The input 202 may include one or more medical images of an anatomical structure. The medical images may be received over the network 120 via the application associated with the system 116 that is running on a computing device, such as imaging computing device 136 and/or user computing device 140. The input 202 may then be pre-processed at step 204. As part of pre-processing, any relevant heath data may be extracted from the medical images (e.g., to de-identify) and the medical images may be converted to a lossless image format, such as portable graphics format (PNG). Additionally, in some examples, the medical images may be fed through a generative adversarial network (GAN) to increase image clarity (e.g., to reconstruct and de-noise the images).

The pre-processed medical images of the anatomical structure may then be provided as input to a trained machine learning model 118A from the plurality of machine learning models 118 stored in storage devices 114. The trained machine learning models 118 may be trained to predict at least one of: a musculoskeletal diagnosis affecting the anatomical structure; an observation associated with one or more objects, such as anatomical features of the anatomical structure, features that are not normally present in the body that may disrupt the body's function, and/or foreign objects inserted into the body; and/or measurements associated with the observations, such as an area or a volume of the features and/or bodies. The observation associated with an object may include identification and/or outlining/visual indication of the object or region of interest, a location of an object, a trajectory of the object, and/or image quality (e.g., is it an optimal image of the given object, such as proper image depth, image focal zone, and image gain, and the recognition of sonographic artifacts including anisotropy, shadowing, refractile shadowing, posterior acoustic enhancement or increased through-transmission, posterior reverberation and ring-down artifact). One or more of the trained machine learning models 118 may also be trained to infer an optimal image frame capture for a given diagnostic or interventional procedure.

The prediction output by the trained machine learning model 118A may then undergo post-processing at step 206 to yield an output 208. Additionally or alternatively (as shown by the dotted lines), the prediction output by the trained machine learning model 118A may be provided as input to another trained machine learning model 118B from the plurality of machine learning models 118 stored in storage devices 114, the output of which may also undergo post-processing at step 206 to yield output 208. While only one or two of the trained machine learning models 118 are depicted in the process 200, in other examples, any number of trained machine learning models may be implemented.

Post-processing at step 206 may generate a result, for example, based on the prediction(s) from the trained machine learning model 118A and/or trained machine learning model to yield the output 208. In other words, the post-processing step 206 transforms the prediction into an informational format and/or display that is consumable by the physician or other healthcare professional. Exemplary informational formats and/or displays may include heatmaps, text overlays superimposed on images, numerical tabular formats, rank ordered tabular formats, text tables, highlight tables, and/or bar charts. In some examples, external (e.g., third party) systems may be utilized to generate the results.

One example result may include visualizations that indicate the prediction within the medical images to assist the physician in performing diagnoses and/or interventions. The system 116 may provide these visualizations for display to the computing device from which the medical images are received, such as the imaging computing device 136 or user computing device 140 via the application. As previously discussed, the medical images may be fed through a GAN at step 204 to increase a clarity of the images input to the trained machine learning models. Additionally or alternatively, the medical images may be fed through a GAN at step 206 to improve the quality of the visualization output to the physician or other healthcare professional.

Another example result generated may include a list of prioritized cases for a physician's attention, e.g., where inferred diagnoses of heightened severity or classification are prioritized. A further example result generated may include a pre-populated written report of the medical image analysis to be reviewed and certified by the physician. Additionally, the result may include generation and transmission of communications that include the medical image analysis to other parties in the clinical setting, such as an original physician, the patient, the patient's caregiver or family members, a surgeon, a physical therapist etc.

Diagnosis Prediction for Musculoskeletal Disorders

Figure 5A:
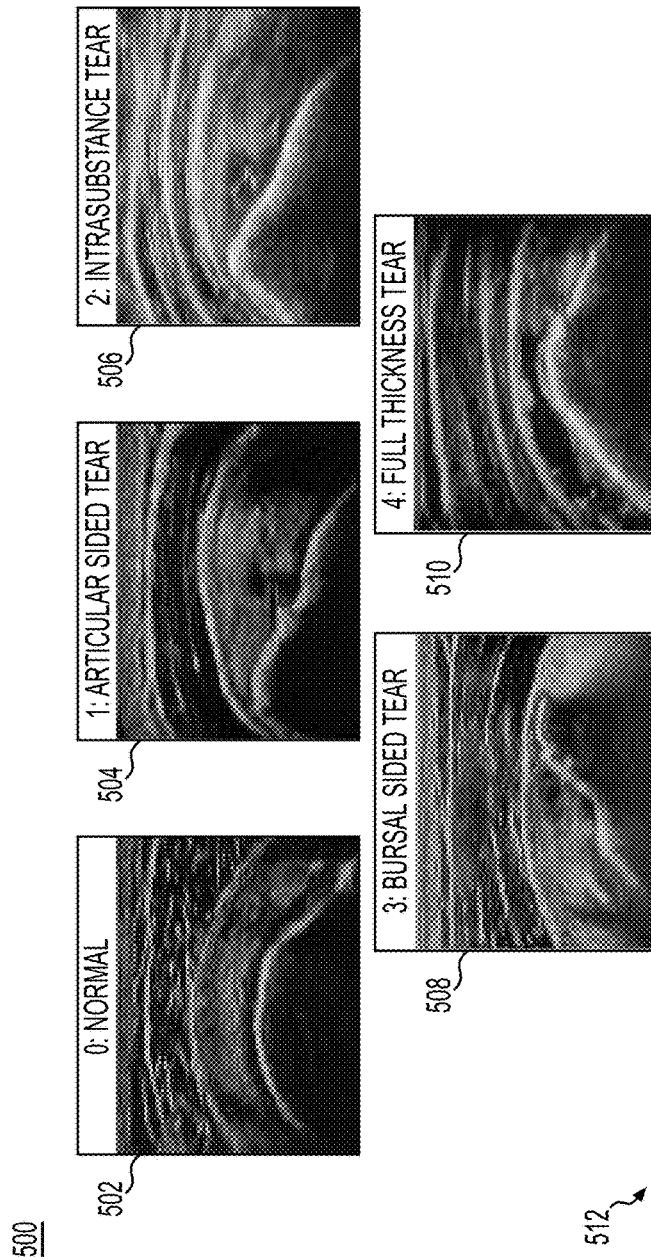
FIG. 5A illustrates a conceptual diagram depicting a training process of a machine learning model to predict a diagnosis for a shoulder injury, according to techniques described herein.
Figure 5B:
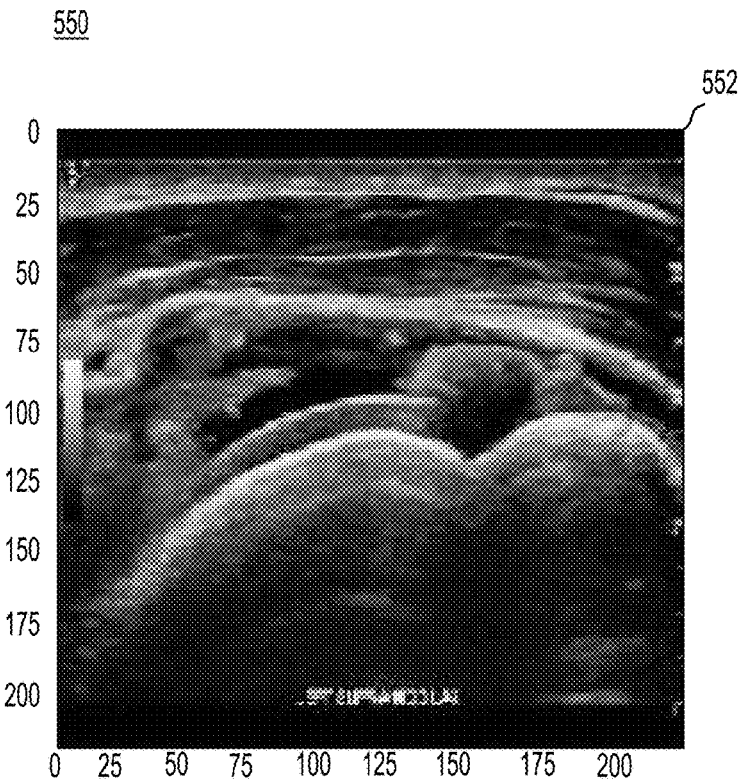
FIG. 5B illustrates an example application user interface displaying a predicted diagnosis for a shoulder injury, according to techniques described herein.

Diagnostic images captured during an examination of a patient may facilitate physician diagnoses of disorders, injuries, and/or conditions, including any classifications thereof (e.g., categories, stages, phases, grades, etc.). Techniques described in FIGS. 3-4 include training and using a machine learning model to diagnose musculoskeletal disorders. FIGS. 5A and 5B describe an exemplary machine learning model trained to diagnose a shoulder injury, such as a rotator cuff tear.

FIG. 3 depicts a flowchart illustrating an exemplary method 300 for training a machine learning model (e.g., one of trained machine learning models 118) to predict a diagnosis of a musculoskeletal disorder, according to exemplary techniques presented herein. Exemplary method 300 (e.g., steps 302-306) may be performed by system 116. Exemplary method 300 may include one or more of the following steps.

At step 302, a plurality of labeled training medical images may be received (e.g., from medical imaging databases 160 over network 120). The training medical images may include ultrasound images of a particular anatomical structure that may be affected by one or more musculoskeletal disorders. The training medical images may be labeled with annotations from physicians that at least indicate one or more musculoskeletal disorders, if any, that are present in the images. The annotations may also indicate anatomical features (e.g., bones, tendons, ligaments, muscles, nerves, etc.) and/or disruptive features that are not normally present in the body and may be associated with the one or more musculoskeletal disorders present in the images. Example disruptive features associated with muscle, ligament, and/or tendon injuries may include hemorrhage, muscle edema, hematoma, fluid collection, lesions, scars, inflammation, defects, tendonosis, ligamentosis, tendonitis, and/or tears. Example disruptive features associated with bone injuries may include stress fractures, avulsion at tendon and ligament attachments, callus formation, fracture nonunion, growth plate injury, and/or screw impingement of tendons. Other exemplary disruptive features may include cellulitis and/or abscesses associated with infection, arthritis (e.g., rheumatoid arthritis, psoriatic arthritis, gout, or osteoarthritis), myositis and diabetic muscle infarction, soft tissue foreign bodies (e.g., wood, plastic, metal, glass, organic and/or plant), peripheral nerve entrapment, soft tissue masses (e.g., lipomas, peripheral nerve sheath tumors, vascular anomalies, ganglion cysts, lymph nodes, and/or malignant soft tissue tumors) and bone masses. Further, the annotations may indicate an area and/or a volume of any of these features. The training medical images may undergo pre-processing (similar to the pre-processing described at step 204 of FIG. 2). In some examples, as part of the pre-processing, the annotations may be extracted or otherwise identified from the training medical images to form labels separate from the training medical images. In other examples, the annotations may be received as labels separate from the training medical images.

For certain types of musculoskeletal disorders, there may be a plurality of classifications for the given type of disorder. Classifications may include categories, stages, phases, grades, and/or the like. For example, and as described in more detail with reference to FIG. 5A, for diagnosing a shoulder injury such as rotator cuff pathology, the rotator cuff may be categorized as normal (e.g., if there is no pathology), tendonitis, tendonosis, calcific tendonitis, calcific tendonosis, delamination, an articular sided tear, an intrasubstance tear, a bursal sided tear, or a full thickness tear. Similar injuries may be categorized for any portion of the anatomy, and training images may contain a plurality of examples of each classification. For example, in addition to shoulder injuries, injuries may be categorized for the elbow, the wrist, the hand, the fingers, the hip, the thigh, the knee, the ankle, the foot, and/or lower leg. If the musculoskeletal disorder of interest includes a plurality of classifications, the labeled training medical images received may be comprised of subsets of labeled training medical images, where each subset may correspond to a respective classification from the plurality of classifications. The corresponding labels for the training medical images in each subset may include annotations that further indicate the known classification from the plurality of classifications for the musculoskeletal disorder that is present in the images.

At step 304, a machine learning model for predicting a diagnosis associated with a musculoskeletal disorder affecting the anatomical structure may be generated and trained using the plurality of labeled training medical images. For example, a training medical image may be input to the machine learning model. The machine learning model may be of any of the example types listed previously herein. The machine learning model may predict a diagnosis associated with the musculoskeletal disorder. In some examples, the predicted diagnosis may be based on a predicted identification of an object relative to a given anatomical structure associated with the musculoskeletal disorder. For example, a predicted diagnosis of calcific tendonitis may be based on a predicted calcium deposit on a tendon of a rotator cuff. The machine learning model may output, for each training image, at least a prediction of whether a musculoskeletal disorder is present. Further, in instances where the predicted diagnosis may be based on a predicted identification of an object relative to a given anatomical structure associated with the musculoskeletal disorder, the predicted object of interest may be output in addition or alternatively to the predicted diagnosis by the machine learning model (e.g., a calcium deposit on the tendon). In other examples, when the disorder includes multiple classifications, the machine learning model may output, for each training image, a score (e.g., a probability) for each classification that represents a likelihood of the training medical image depicting the respective classification for the musculoskeletal disorder.

To train the machine learning model, the predicted diagnosis associated with the musculoskeletal disorder output by the machine learning model for a training medical image may be compared to the label corresponding to the training medical image to determine a loss or error. For example, a predicted diagnosis for a first training image may be compared to the known diagnosis within the first training image identified by the corresponding label. The machine learning model may be modified or altered (e.g., weights and/or bias may be adjusted) based on the error to improve the accuracy of the machine learning model. This process may be repeated for each training image or at least until a determined loss or error is below a predefined threshold. In some examples, at least a portion of the training images and corresponding labels may be withheld and used to further validate or test the trained machine learning model.

To provide an illustrative example, FIG. 5A is a conceptual diagram 500 illustrating a training process of a machine learning model to predict a diagnosis for a shoulder injury. For diagnosing a shoulder injury, such as a rotator cuff tear, the rotator cuff tear may be categorized as normal (e.g., if there is no tear), an articular sided tear, an intrasubstance tear, a bursal sided tear, or a full thickness tear. Accordingly, labeled training medical images used to generate and train a machine learning model to predict a diagnosis for a rotator cuff tear may be comprised of subsets of labeled training medical images corresponding to each respective category. For example, a first subset 502 may include images of shoulders without a rotator cuff tear, a second subset 504 may include images of shoulders with an articular sided tear, a third subset 506 may include images of shoulders with a bursal sided tear 508, and a fourth subset 510 may be comprised of images of shoulders may include images of shoulders with a full thickness tear. Exemplary numbers of images included in each of the above-described subsets and the representation (e.g., percentage) of each subset among the total images are depicted in table 512. The table 512 also includes a breakdown of the number of images within each subset used in the training set versus the number withheld for the validation set.

Returning to FIG. 3, once the machine learning model is sufficiently trained, at step 306, the trained machine learning model may be stored for subsequent use (e.g., as one of trained machine learning models 118 stored in storage devices 114). In some examples, the trained machine learning model may be a single machine learning model that is generated and trained to predict diagnosis of a plurality of different musculoskeletal disorders that affect a given anatomical structure. In other examples, the exemplary method 300 may be performed to generate and train an ensemble of machine learning models, where each model predicts a diagnosis of a particular musculoskeletal disorder that affects the given anatomical structure (e.g., one model for identifying rotator cuff tear, one model for identifying calcific tendonitis in the rotator cuff, and so on). When deployed to evaluate a medical image of the anatomical structure, the ensemble of machine learning models may be run in parallel.

FIG. 4 depicts a flowchart illustrating an exemplary method 400 for predicting a diagnosis of a musculoskeletal disorder, according to exemplary techniques presented herein. Exemplary method 400 (e.g., steps 402-408) may be performed by the system 116. Exemplary method 400 may include one or more of the following steps.

At step 402, a medical image of an anatomical structure may be received from a computing device. The medical image may be an ultrasound image, or of any imaging modality discussed herein, and the computing device may include the user computing device 140 or the imaging computing device 136 of the ultrasound imaging system 132. For example, the computing device may be executing an application associated with the medical image processing system 110 (e.g., a client application). In some aspects, the medical image may be a previously captured and stored image that is selected from local storage of the computing device or a remote data storage system (e.g., PACs system 150) and transmitted via the application to the system 116. In other aspects, the medical image may be a live image that is being captured in real-time (e.g., by the ultrasound imaging system 132 as a patient is being imaged) and is transmitted via the application to the system 116. In some examples, the user may also select, via a user interface of the application, a type of musculoskeletal disorder that may be affecting the anatomical structure captured in the medical image. The type of musculoskeletal disorder may be selected based on symptoms reported by a patient and/or signs detected by the physician upon a physical examination and/or an initial review of the medical image.

At step 404, the medical image may be provided as input to a trained machine learning model for predicting a diagnosis associated with a musculoskeletal disorder affecting the anatomical structure, such as the machine learning model trained using method 300 described with reference to FIG. 3. In examples where the exemplary method 300 is used to generate and train an ensemble of machine learning models, the medical image may be provided as input to each machine learning model of the ensemble of machine learning models running in parallel. In some examples, when the type of musculoskeletal disorder is selected by the physician, only the machine learning model trained to identify the type of musculoskeletal disorder may be run (e.g., to conserve computing resources).

At step 406, a predicted diagnosis may be received from the trained machine learning model. In some examples, the predicted diagnosis may include at least an indication of a presence or absence of a musculoskeletal disorder in the medical image. For musculoskeletal disorders with classifications, the predicted diagnosis may also indicate the predicted classification. Additionally or alternatively, in examples where the predicted diagnosis may be based on a predicted identification of an object relative to a given anatomical structure associated with the musculoskeletal disorder, the predicted diagnosis may include the predicted object that was identified (the identification of the object discussed in more detail below). Additionally or alternatively, the predicted diagnosis may have an associated score, representing a confidence associated with the prediction. Similarly, if the musculoskeletal disorder includes classifications, the predicted diagnosis may include a score for each classification that represents a likelihood of the medical image depicting the respective classification for the musculoskeletal disorder, where the classification having the highest score may be the predicted diagnosis.

At step 408, the medical image and the predicted diagnosis may be provided to the computing device for display. For example, the medical image and the predicted diagnosis may be received via the application executing on the computing device (e.g., user computing device 140 and/or imaging computing device 136) and displayed within a user interface of the application, such as the exemplary user interface shown in FIG. 5B.

FIG. 5B depicts an example application user interface 550 displaying a predicted diagnosis for a shoulder injury. The application user interface 550 may be a user interface of the application associated with the system 116 that is executing on a computing device, such as user computing device 140 and/or imaging computing device 136. One of the plurality of machine learning models 118 may be generated and trained to predict a diagnosis for a rotator cuff tear using the exemplary training medical images described with reference to FIG. 5A. A medical image, such as medical image 552 of a rotator cuff of a shoulder, may be received for processing by the system 116 (e.g., using exemplary method 400). The medical image 552 may include the tissues, muscles, and tendons of the rotator cuff structure, and specifically the supraspinatus muscle/tendon complex. Once processed, the system 116 may provide at least the medical image 552 and the predicted diagnosis 554 to the application for display in the application user interface 550. For example, the predicted diagnosis 554 may indicate a tear and include a predicted classification of a full thickness tear.

Additionally, a score 556 associated with the predicted diagnosis 554 may be displayed. The score 556 may indicate a likelihood or probability that the predicted diagnosis 554 for the musculoskeletal disorder is present within the medical image 552. The score 556 may assist a physician in the diagnosing process. For example, a physician may feel more confident in using the predicted diagnosis 554 as one factor in the diagnosing process when there is a high value for the score 556 for the predicted diagnosis 554 that corresponds (or at least not contradict) what the physician is able to visualize with their own eyes. Additionally, for musculoskeletal disorders like a rotator cuff tear that have a plurality of classifications (e.g., categories), a table 558 or other similar graphical element listing each of the classifications 560 and associated scores 562 may be displayed on user interface 550. For example, as shown in table 558, a respective score that the medical image 552 depicts a normal rotator cuff (no tear), an articular sided tear, an intrasubstance tear, a bursal sided tear, or a full thickness tear may be included for display.

The application user interface 550 described above is provided merely as an example, and may include additional, fewer, different, or differently arranged information than depicted in FIG. 5B.

The general technique for musculoskeletal disorder diagnosis described above with reference to FIGS. 3-5B may have many possible specific applications or use cases, as described below in more detail. For example, a similar technique may be used to identify objects within medical images to facilitate (guide) orthopedic surgery in joints, muscles, tendons and ligaments. Additionally or alternatively, the technique above may be used in non-surgical orthopedics or Osteopathic Manipulative Treatment which may include therapeutic techniques by the clinician (such as stretching, gentle pressure and resistance) as applied by the treating physician on the patient. While ultrasound images are the image modality input to the trained machine learning model in the technique above, in other techniques, a digital image from another medical imaging modality, such as images from a CT scanner, an X-Ray image, etc., may be used to diagnose injuries in other areas of a patient's body, such as brain injuries, bone injuries, etc.

Diagnostic or Interventional Observations: Object Identification, Measurement, and Visualization Techniques described in FIGS. 6-7 include training and using a machine learning model to identify objects within a medical image of an anatomical structure. Objects may include anatomical features of the anatomical structure, features that are not normally present in the body that may disrupt the body's function, and/or foreign objects that are inserted during a procedure, for example. Object identification may be useful for diagnostics, as well as when guiding interventions post-diagnosis. Additionally, for billing purposes, physicians may be required to submit images having certain objects identified therein to provide proof of a given procedure. For example, when performing a needle biopsy procedure, an image including the needle identified therein may be submitted as part of the billing documents.

Once objects are identified, measurements associated with the objects, such as an area and/or a volume of the objects, may also be determined. Measurements may be helpful to a physician in determining whether pathology is normal and abnormal, and may be used in the diagnosing process for a musculoskeletal disorder. Additionally, by obtaining measurements of the object of interest over time (e.g., during subsequent patient visits), a patient's progression and/or regression associated with a musculoskeletal disorder may be tracked by the physician. For example, for carpal tunnel, an area of the median nerve may be a useful indicator for diagnosis, and can be monitored over time to determine if the carpal tunnel is regressing (e.g., post-treatment). As another example, for a rotator cuff tear, a volume of tendon that is separated from bone may be monitored over time to determine if the injury is regressing (e.g., post-treatment). As a further example, after identifying a disruptive feature that is not normally present in the body and may disrupt the body's function, such as a ganglion cyst, an effusion, a calcium deposit, a mass, a lesion, or the like, at least a portion of the structure may be surgically removed and post-surgery images may be captured. Measurements for this feature in the pre-surgery and post-surgery images can be automatically compared by the system to provide objective evidence of how much of the object of interest was removed. For example, images from a prior imaging session may be automatically co-registered with images from a current imaging session. A plurality of co-registration points may be automatically identified, and the corresponding object, which may be indicated in at least one of the image sets by a user, may be identified in both sets of images, past and current. A calcium deposit in the prior set of images may be automatically associated with the same calcium deposit in the current imaging session, and measurements may be automatically taken to determine progression or regression of disease. In some instances the object, such as a cyst or mass, may be gone entirely from images of the current session due to a surgery or other procedure. In this case, the system may automatically determine that an object that was an object of interest in the prior imaging session is no longer present.

In some examples, the identified objects may be input to another process. For example, as described in FIGS. 8-9, a machine learning model may be trained and used to determine whether the medical image is an optimal image for the identified object (e.g., is an optimal viewing angle for the object), and predict an orientation of the probe capturing the image that resulted in the viewing angle. If the medical image is not optimal, a suggested probe movement to capture a more optimal image for the identified object of interest may be determined based on the predicted probe orientation (e.g., a current probe orientation) and a learned probe orientation associated with optimal image capture.

Further, as shown and described with reference to FIG. 10, a visualization to indicate the identified objects and any measurements associated with the objects may be provided for display. Additionally, if the medical image is determined to not be optimal for one or more of the identified objects, the visualization may further include directional indicators indicating the suggested probe movement to capture a more optimal image.

Returning to FIG. 6, the flowchart illustrates an exemplary method 600 for training a machine learning model (e.g., one of trained machine learning models 118) to identify objects within a medical image of an anatomical structure, according to exemplary techniques presented herein. Exemplary method 600 (e.g., steps 602-606) may be performed by the system 116. Exemplary method 600 may include one or more of the following steps.

At step 602, a plurality of labeled training medical images may be received (e.g., from medical imaging databases 160 over the network 120). The training medical images may include ultrasound images of a particular anatomical structure. The training medical images may be labeled with annotations from physicians that indicate a plurality of objects within the respective images. The annotated objects may include anatomical features of the anatomical structure, such as bones, tendons, ligaments, cartilage, muscles, nerves, veins, arteries, etc. The annotated objects may also include features that are not normally present in the anatomical structure that may disrupt the body's function (e.g., disruptive features), such as ganglions, calcium deposits, effusions, tears, masses, lesions, restrictions, impingements, compressions, etc. The annotated objects may further include foreign bodies, such as an inflatable balloon, needle, knife, scalpel, finger, stent, intravascular device, catheter, surgical instrument, etc. that may be inserted into the body as part of a procedure. Further, the annotations may indicate an area and/or a volume of any of the above-described objects. The training medical images may represent a variety of different types of objects. For example, a first subset of training images may include ganglions, a second subset may include calcium deposits, a third set may include inflatable balloons, a fourth set may include needles, etc. In some examples, the training medical images may further be labeled with annotations that indicate measurements associated with one or more of the objects in the respective images. For example, an image may be annotated with an area and/or volume of an object. In instances where a volume of an object is annotated for a given object, for a given training image there may be an image sequence subset, where each image within an image sequence subset may be captured at different depth and frequency settings of the ultrasound imaging system 132 without moving a position of the probe 134.

The training medical images may undergo pre-processing (similar to the pre-processing described at step 204 of FIG. 2). In some examples, as part of the pre-processing, the annotations may be extracted or otherwise identified from the training medical images received to form labels separate from the training medical images. In other examples, the annotations may be received as labels separate from the training medical images. The corresponding labels for the training medical images may include the known types of each of the objects annotated.

At step 604, a machine learning model for identifying objects may be generated and trained using the plurality of labeled training medical images. For example, a training medical image may be input to the machine learning model. The machine learning model may identify one or more objects within the training medical image. In some examples, the machine learning model may also predict measurements (e.g., an area and/or a volume) associated with an object.

To train the machine learning model, the output by the machine learning model for a training medical image may be compared to the label corresponding to the training medical image to determine a loss or error. For example, object(s) identified within a first training image may be compared to the known object types identified by the corresponding label. Additionally, when the prediction includes measurements associated with the object(s) identified, the measurements predicted for the objects identified within the first training image may be compared to the known measurements of the known object types included the first training image identified by the corresponding label. The machine learning model may be modified or altered (e.g., weights and/or bias may be adjusted) based on the error to improve an accuracy of the machine learning model. This process may be repeated for each training image or at least until a determined loss or error is below a predefined threshold. In some examples, at least a portion of the training images and corresponding labels may be withheld and used to further validate or test the trained machine learning model.

Once the machine learning model is sufficiently trained, at step 606, the trained machine learning model may be stored for subsequent use (e.g., in storage device 114). In some examples, the trained machine learning model may be a single machine learning model that is generated and trained to identify each of the different types of objects that may be present within a medical image of the anatomical structure. In other examples, the exemplary method 600 may be performed to generate and train an ensemble of machine learning models, where each model identifies a particular type of object (e.g., one system for identifying ganglions, another system for identifying calcium deposits, and so on). When deployed to evaluate a medical image of the anatomical structure, the ensemble of machine learning models may be run in parallel.

FIG. 7 depicts a flowchart illustrating an exemplary method 700 for identifying objects within a medical image of an anatomical structure, according to exemplary techniques presented herein. Exemplary method 700 (e.g., steps 702-708) may be performed by the system 116. Exemplary method 700 may include one or more of the following steps.

At step 702, a medical image of an anatomical structure may be received from a computing device. The medical image may be an ultrasound image, and the computing device may include the user computing device 140 or the imaging computing device 136 of the ultrasound imaging system 132. For example, the computing device may be executing an application associated with the medical image processing system 110 (e.g., a client application). In some aspects, the medical image may be a previously captured and stored image that is selected from local storage of the computing device or a remote data storage system (e.g., PACs system 150) and transmitted via the application to the system 116. In other aspects, the medical image may be a live image that is being captured in real-time (e.g., by the ultrasound imaging system 132 as a patient is being imaged) and is transmitted via the application to the system 116. In some examples, more than one medical image may be received (e.g., an image sequence subset of the anatomical structure captured at various depth and frequency combinations may be received).

In some examples, the physician may also select, via a user interface of the application, one or more particular types of objects that they would like to confirm are present and/or would like to distinguish between in the image. As one illustrative example, for certain surgeries, an inflatable balloon may be inserted into the body that is filled with a fluid, such as saline, to inflate the balloon during the surgery. To an eye of a physician, it may be difficult to distinguish between the balloon and another feature, such as a ganglion, in an ultrasound image. Accordingly, the physician may select a balloon as a particular object of interest to facilitate guiding of a needle to fill the balloon (and not a feature like a ganglion) with fluid during the surgery. For example, upon receiving the physician's selection, the balloon (and not the ganglion) may be visually emphasized (e.g., highlighted) along with the needle, where the needle may visualized in a similar but distinguishable manner from the balloon (e.g., highlighted in a different color), and thus represent to the viewer the relative positions and/or orientations of the balloon and the needle.

At step 704, the medical image may be provided as input to a trained machine learning model (e.g., one of trained machine learning models 118), such as the trained machine learning model trained using method 600 described with reference to FIG. 6. In examples where the exemplary method 600 is used to generate and train an ensemble of machine learning models, the medical image may be provided as input to each machine learning model of the ensemble of machine learning models running in parallel. In some examples, when one or more particular types of objects of interest are selected by the physician, only the machine learning models trained to identify those particular types of objects of interest may be run (e.g., to conserve computational resources).

At step 706, a prediction of one or more objects identified may be received from the trained machine learning model. Additionally, the prediction may have an associated score, representing a confidence associated with the prediction (e.g., a likelihood that each type of object identified is actually the object in the medical image). In some examples, the machine learning model may also be trained to output measurements, such as an area and a volume, associated with one or more of the identified objects. The area may represent a cross-sectional area of an object, and the system may instruct the user to move the probe 134 in order to obtain the optimal angle to obtain a cross-sectional area. In instances where the volume of one or more of the identified objects is predicted, multiple medical images may be received at step 702 and input to the model at step 704 (e.g., the image sequence subset of the anatomical structure captured at various depth and frequency combinations) to enable volume prediction. In such examples, the prediction may also include predicted measurements associated with identified objects.

At step 708, an indication of the prediction may be provided to the computing device for display (e.g., via the application executing on computing device 140 and/or imaging computing device 136). For example, a visualization may be generated based on the prediction at post-processing step 206 described with reference to FIG. 2. The visualization may label, highlight, or otherwise emphasize the objects identified within the medical image, and the visualization may be provided for display within the application user interface. Additionally, the visualization may include the score associated with the prediction for each object. Further, the visualization may include any measurements associated with one or more of the identified objects. An exemplary visualization is shown in FIG. 10 below.

As discussed above, in some examples, the machine learning model may be trained to output measurements, such as an area and a volume, associated with one or more of the identified objects In other examples, measurements associated with a given object identified may be obtained independently of the prediction received at step 706. As one non-limiting example, in some aspects, the visualization provided to the computing device (e.g., at step 708) may also include a tracer tool control element within the application user interface. The tracer tool control element may be selectable by the physician viewing the medical image to trace along a boundary of an object in the displayed medical image. The system 116 may then be able to determine the area of the object using the traced boundary, and provide the area of the object to the computing device for display.

As another non-limiting example, in some aspects, volume sweep imaging may be implemented to determine a volume of an object. For example, a plurality of ultrasound images of the anatomical structure captured at varying depths and frequencies may be received as two-dimensional (2D) slices with a location and an orientation. The system 116 may reconstruct a three-dimensional (3D) visualization of the object using the 2D slices, and the volume of the object may be determined from the 3D visualization. The volume may then be provided to the computing device for display.

Additionally, in some examples, after displaying the visualization of the medical image with the identified object(s), the operator may select to place a visual lock on one of the identified objects (e.g., an object of interest to a user) such that when the operator moves the probe, the identified object remains labeled, highlighted, or otherwise emphasized within a new medical image post-probe movement. For example, the operator may provide touch input to the display of the computing device in an area of the medical image corresponding to the object to be locked. A position of the object relative to a probe location capturing the medical image (e.g., a current probe location) may be identified for use as a reference. The object may be static, therefore, by knowing a first position of the object relative to the probe prior to the probe's motion (e.g., the reference) and determining a motion of the probe, a second position of the object relative to the probe's motion may be determined. The motion of the probe may be detected using sensors attached to the probe, such as accelerometers, gyroscopes, and/or inertial sensors. The identified object may be labeled, highlighted, or otherwise emphasized at the second position within the new medical image post-probe movement. For example, the identified object visually locked may be a lesion or mass that is to be removed as part of an ultrasound-guided surgery. Resultantly, as the probe is moved during the procedure, the lesion or mass continues to be labeled, highlighted, or otherwise emphasized to enable the surgeon to maintain a view of the lesion or mass.

FIG. 8 depicts a flowchart illustrating an exemplary method 800 for training a machine learning model (e.g., one of trained machine learning models 118) to identify an optimal image for an identified object within a medical image of an anatomical structure, according to exemplary techniques presented herein. Exemplary method 800 (e.g., steps 802-806) may be performed by system 116. Exemplary method 800 may include one or more of the following steps.

At step 802, a plurality of labeled training medical images of an anatomical structure may be received (e.g., from medical imaging databases 160 over the network 120). The trained medical images may include a plurality of objects annotated within the image. The annotated objects may include anatomical features of the anatomical structure, such as bone, tendons, ligaments, cartilage, muscles, nerves, vein, arteries, etc. The annotated objects may also include features that are not normally present in the anatomical structure that may disrupt the body's function, such as ganglions, calcium deposits, effusions, tears, masses, lesions, restrictions, impingements, compressions, etc. The annotated objects may further include foreign bodies, such as an inflatable balloon, needle, knife, scalpel, finger, stent, intravascular device, catheter, surgical instrument etc. that may be inserted into the body as part of a procedure.

The trained medical images may represent a variety of different types of objects that are annotated within the images. For a given object type, a subset of the training medical images including that given object type may be comprised of images with a plurality of different viewing angles of the object within the image (e.g., the different viewing angles based on an orientation of a probe of the imaging system used to capture the image). Certain viewing angles may be more optimal than others for the object type based on the presence or absence of musculoskeletal ultrasound artifacts, such as anisotropy, posterior enhancement or shadowing, edge artifacts, etc. Using anisotropy as an example, a tissue is anisotropic if the properties of the tissue change when measured from different viewing directions. For example, when a tendon or a ligament is imaged perpendicular to the ultrasound beam, the characteristic hyperechoic (visually displayed as light gray in color) fibrillar appearance can be seen. However, when the ultrasound beam is angled 2 to 3 degrees relative to the long axis of the tendon, the normal hyperechoic (light gray color) is lost, and the tendon becomes more hypoechoic (dark gray) as the angle increases. Once a tendon is identified anisotropy may be corrected to exclude pathology.

The training medical images may also have corresponding ground truth labels. For example, each image may be labeled as being a known optimal image or a known non-optimal image of the object type. In some examples, the ground truth labels may also include a known orientation of the probe when the training medical image was captured. The training medical images may also undergo pre-processing (similar to the pre-processing described at step 204 of FIG. 2).

At step 804, a machine learning model for predicting whether a medical image is an optimal image of an object identified within the medical image may be generated and trained using the plurality of labeled training medical images. In some examples, the machine learning model may also be generated and trained to predict an associated probe orientation used to capture the medical image. To train the machine learning model, the prediction output by the machine learning model for the training medical image may be compared to the ground truth label(s) corresponding to the training medical image to determine a loss or error. For example, a prediction of optimal or non-optimal image for a first training medical image may be compared to the corresponding ground truth label for the training medical image as being a known optimal image or a known non-optimal image of an object therein. Additionally, when the prediction output also includes the predicted orientation of the probe, the predicted orientation may be compared to the known orientation of the probe included in the corresponding ground truth label. The machine learning model may be modified or altered (e.g., weights and/or bias may be adjusted) based on the error to improve an accuracy of the machine learning model. This process may be repeated for each training image or at least until a determined loss or error is below a predefined threshold. In some examples, at least a portion of the training images and corresponding labels may be withheld and used to further validate or test the trained machine learning model.

Once the machine learning model is sufficiently trained, at step 806, the trained machine learning model may be stored for subsequent use (e.g., as one of trained machine learning models 118 stored in storage devices 114). In some examples, the trained machine learning model may be a single machine learning model that is generated and trained to predict whether a medical image of the anatomical structure is an optimal image of a plurality of different object types that may be contained therein. In other examples, the exemplary method 800 may be performed to generate and train an ensemble of machine learning models, where each model predicts whether a medical image of the anatomical structure is an optimal image of a particular object type that is identified therein. When deployed to evaluate a medical image of the anatomical structure, the ensemble of machine learning models may be run in parallel. In some examples, when the particular object type of the object is identified (e.g., is received as output of another process such as method 700), only the machine learning model trained to predict whether a medical image of the anatomical structure is an optimal image of the particular object type may be run to conserve computing resources.

FIG. 9 depicts a flowchart illustrating an exemplary method 900 for determining whether a medical image is an optimal image of an object identified therein, according to exemplary techniques presented herein. Exemplary method 900 (e.g., steps 902-912) may be performed by the system 116. Exemplary method 1900 may include one or more of the following steps At step 902, a medical image of an anatomical structure may be received from a computing device. The medical image may be an ultrasound image, and the computing device may include the user computing device 140 or the imaging computing device 136 of the ultrasound imaging system 132. For example, the computing device may be executing an application associated with the medical image processing system 110 (e.g., a client application). In some examples, the medical image may be a previously captured and stored image that is selected from local storage of the computing device or a remote data storage system (e.g., PACs system 150) and transmitted via the application to the system 116. In other examples, the medical image may be a live image that is being captured in real-time (e.g., by the ultrasound imaging system 132 as a patient is being imaged) and is transmitted via the application to the system 116. In some examples, the user may also select, via a user interface of the application, one or more particular types of objects that they would like to confirm are present and/or would like to distinguish between in the medical image.

At step 904, the medical image may be provided as input to a first trained machine learning model to obtain a prediction of one or more objects identified (e.g., as output of the first trained machine learning model). The first trained machine learning model may be a machine learning model trained and used for identifying objects within a medical image of the anatomical structure described with reference to FIGS. 6 and 7. For example, the first trained machine learning model may predict that objects identified within the ultrasound image include a calcium deposit located on a tendon of the shoulder.

At step 906, the medical image may be provided to a second trained machine learning model for identifying whether the medical image is an optimal image of the object(s) identified (e.g., the particular type of objects identified and received as a prediction from the first trained machine learning model). The second trained machine learning model may be the trained machine learning model trained using method 800 described with reference to FIG. 8. Continuing the above example, where objects identified include a calcium deposit located on a tendon of the shoulder, the second trained machine learning model may be trained to at least identify optimal images of calcium deposits.

At step 908, a prediction of whether the medical image is an optimal image of the object(s) identified may be received as output of the second trained machine learning model. In some examples, the prediction output may also include a predicted orientation of the probe capturing the medical image (e.g., a current probe orientation resulting in a viewing angle of the object(s) identified that is either optimal or non-optimal).

At step 910, an indication of the prediction may be provided to the computing device for display. For example, a visualization may be generated based on the prediction at post-processing step 206 described with reference to FIG. 2. In some examples, if the medical image is predicted as being an optimal image of the object(s) identified, instructions may be provided to the computing device to cause display of a positive visual indicator in conjunction with the medical image. In other examples, if the medical image is predicted as being a non-optimal image of the identified object(s), instructions may be provided to the computing device to cause display of a prompt for the operator to make probe adjustments (e.g., reorient the probe) to allow capture of an optimal image of the identified object(s).

The prompt may include directional instructions to guide the operator to adjust a current orientation of the probe corresponding to the predicted orientation in order to achieve an optimal image capture. For example, as part of the training, the trained machine learning model may learn a probe orientation associated with an optimal viewing angle (e.g., resulting in an optimal image) of the identified object(s) of the respective types from the labeled training medical images. Accordingly, the learned probe orientation associated with optimal image capture of the identified object(s) of the particular types may be compared to the current probe orientation to generate directional instructions to adjust the current probe orientation to the learned probe orientation. In some examples, the directional instructions may be in the form of probe direction indicators, as shown with reference to FIG. 10.

Figure 10:
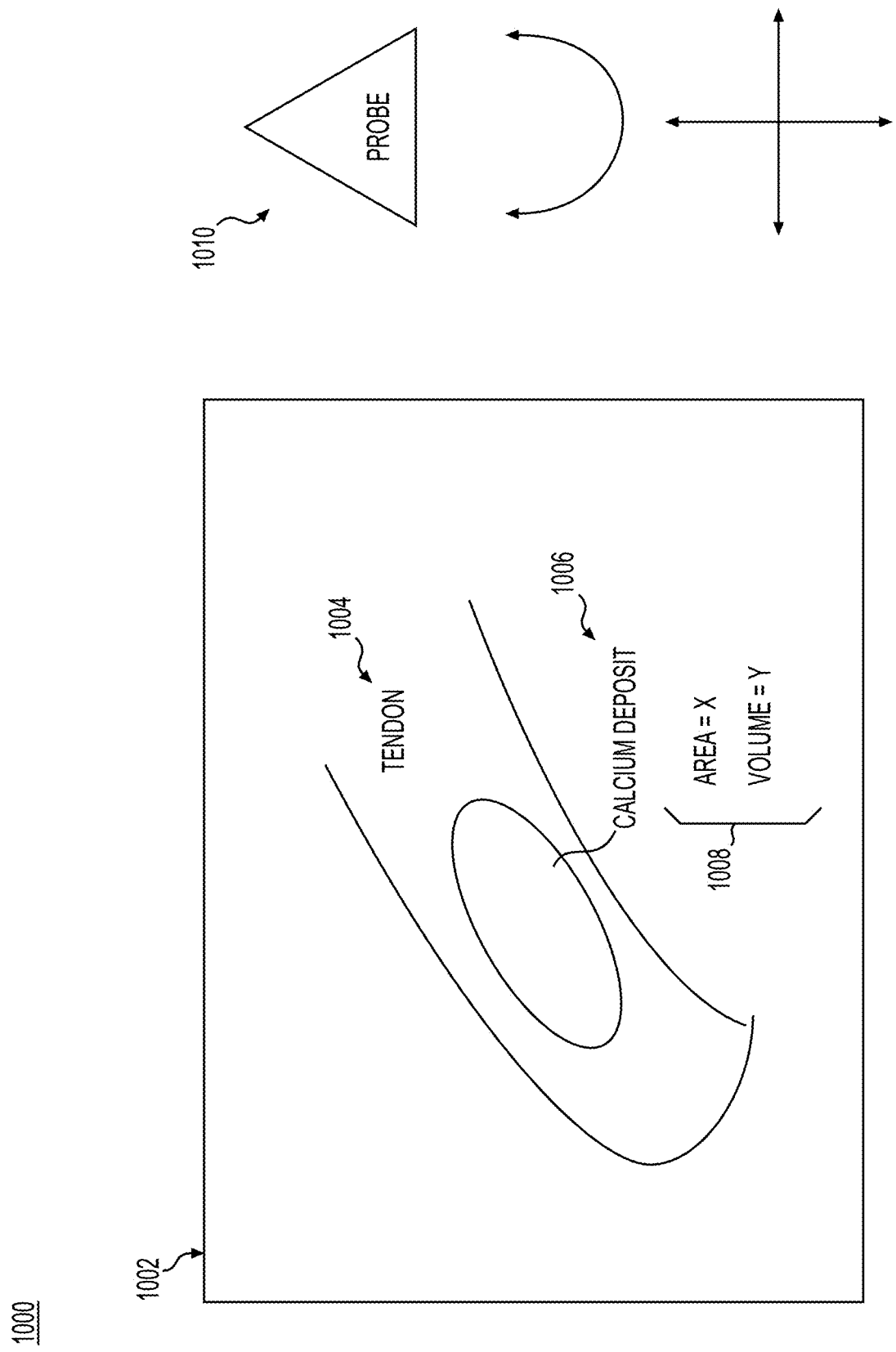
FIG. 10 illustrates an example application user interface displaying objects identified within a medical image, which may be displayed in accordance with techniques presented herein.

FIG. 10 is an example application user interface 1000 displaying objects identified in a medical image and associated object measurements. The application user interface 1000 may be a user interface of the application that is displayed on the user computing device 140 and/or imaging computing device 136. A machine learning model, such as the machine learning model trained using the exemplary method 600 described with reference to FIG. 6, may be generated and trained to identify objects within ultrasound images of shoulder joints.

An ultrasound image of a patient's shoulder may be received from the application for processing by the system 116 (e.g., using exemplary method 600) to identify a tendon 1004 (e.g., an anatomical feature) and a calcium deposit 1006 (e.g., a feature not normally present in the body that may disrupt the body's function), among other objects within the ultrasound image. Once processed, the system 116 may provide the application with a visualization including at least the medical image 1002 with the tendon 1004 and the calcium deposit 1006 labeled, highlighted, or otherwise emphasized therein for display via the application user interface 1000.

Additionally, measurements 1008 associated with one or more of the objects identified, such as the calcium deposit 1006, that are either obtained as additional output of the trained machine learning model or are obtained independently (e.g., using the above-described tracing to obtain an area and/or volumetric sweep imaging techniques to obtain a volume) may be displayed. In some examples, and as shown, the measurements 1008 may be displayed as annotations of the medical image 1002 in conjunction with calcium deposit 1006.

Further, the application user interface 1000 may include probe direction indicators 1010 that suggest a direction for moving the probe 134 of the ultrasound imaging system 132 to capture a more optimal image of the calcium deposit 1006, for example, than the current image displayed. The determination of whether the medical image 1002 is an optimal image of the calcium deposit 1006, and if not, the determination of the suggested direction for movement of the probe may be obtained using a process similar to exemplary method 900 described with reference to FIG. 9. The probe direction indicators 1010 may include arrows that indicate for an operator of the ultrasound imaging system 132 to slide the probe 134 (e.g., forward, backward, right, or left) and/or rotate the probe 134. In some examples, the probe direction indicators 1010 may be animated such that an arrow pointing in the direction of the suggested movement may be highlighted, flashed, or otherwise visually brought to the attention of the user.

The application user interface 1000 described above is provided merely as an example, and may include additional, fewer, different, or differently arranged information than depicted in FIG. 10.

Interventional Observations: Predictions and Visualizations of Instrument Location and Trajectory A physician may utilize electronic medical images during a procedure to e.g., visualize an instrument inserted into the patient's body to assist the physician in safely guiding the instrument to an intended target area. An instrument may include any device, tool, or object that is inserted into the body as part of a procedure, such as a treatment or a surgery. For example, the physician may insert a needle of a medication syringe containing a steroid into a muscle of the shoulder as part of a treatment to reduce pain. In such examples, ultrasound imaging may be used by the physician to guide the needle into a specific area of the muscle. Additionally, ultrasound-guided surgery is becoming increasingly common. For example, an ultrasound guided needle biopsy of the shoulder may be performed to remove at least a portion of a mass identified within the shoulder to determine if the mass is cancerous, pre-cancerous, or benign.

Often an important part of the instrument to locate is a distal end of the instrument (e.g., the tip, or end of the instrument furthest away from an operator) that is used to perform a given action on a target area of the body. For example, for a needle biopsy, the distal end of the instrument may be the tip of the biopsy needle that removes tissue from a target area, such as a mass or lesion. Accordingly, a precise location of the distal end may be necessary to prevent the distal end from acting on a different, non-target area of the body (e.g., to prevent puncturing a neighboring organ). Currently, for an operator of an ultrasound imaging device to locate a distal end of an instrument, the operator has to manually manipulate a probe of the imaging device (e.g., by rotating, sliding, or heel-toeing the probe) until the position of the probe captures an image in which the operator can see where the distal end of the instrument is inside the body. The operator may have to repeatedly perform these manipulations as the instrument is advanced toward the target to continue to visualize the distal end of the instrument.

Figure 15:
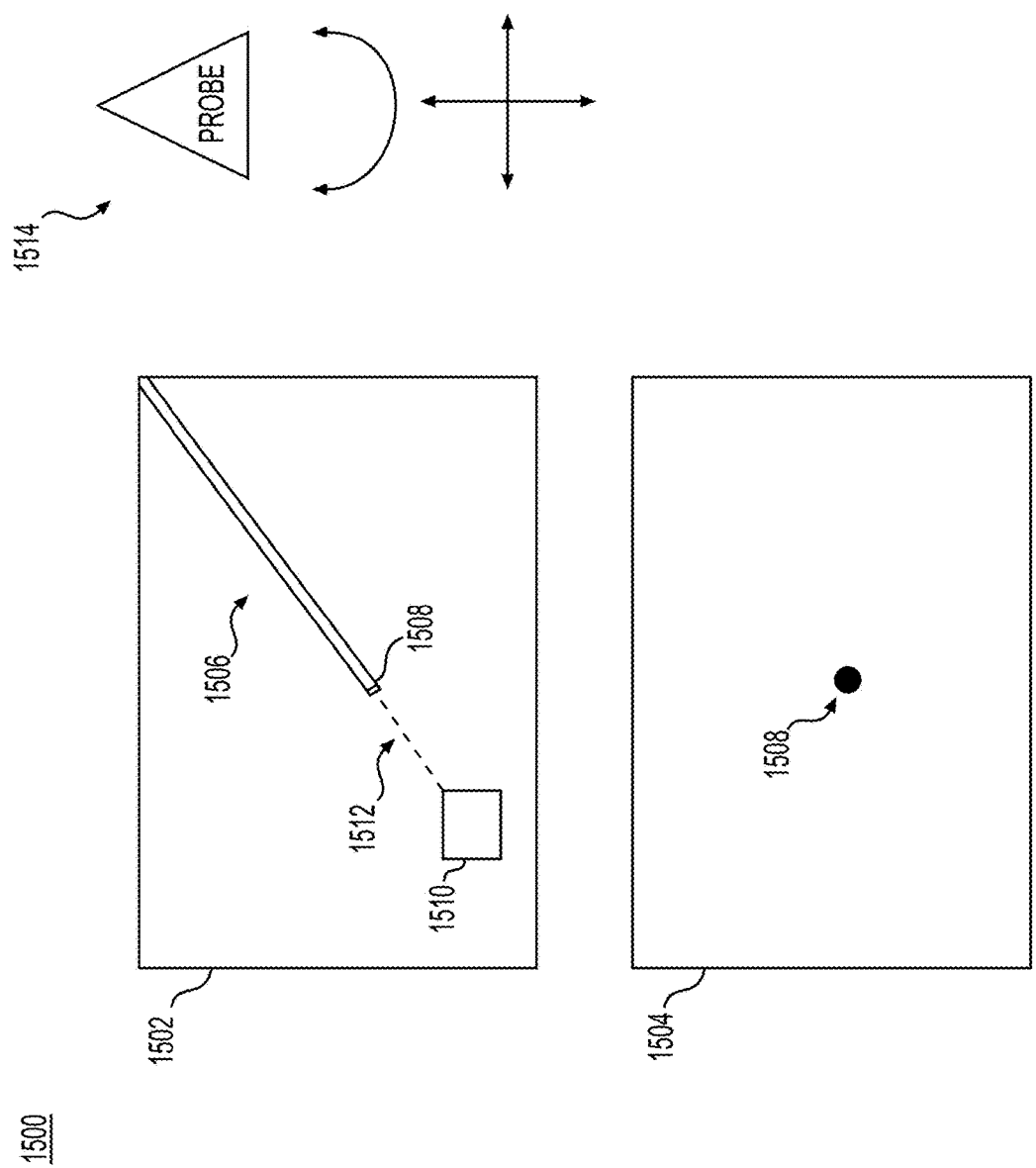
FIG. 15 illustrates an example application user interface displaying a predicted instrument location and trajectory, according to techniques described herein.

To improve upon the current manual techniques, techniques presented in FIGS. 11-12 describe training and use of a machine learning model that, based on an input medical image, predicts a location of an instrument (e.g., in real-time) during a procedure. Additionally, as described in FIGS. 13-14, another machine learning model may be trained and used to predict a trajectory of the instrument to an intended target. A visualization including the predicted location and the trajectory of the instrument overlaid on the medical image, among other information, may be displayed to the physician, as shown in FIG. 15.

FIG. 11 depicts a flowchart illustrating an exemplary method 1100 for training a machine learning model (e.g., one of trained machine learning models 118) to predict a location of an instrument, according to exemplary techniques presented herein. Exemplary method 1100 (e.g., steps 1102-1106) may be performed by the system 116. Exemplary method 1100 may include one or more of the following steps.

At step 1102, a plurality of training medical images may be received (e.g., from medical imaging databases 160 over the network 120). The training medical images may include ultrasound images of an anatomical structure in which an instrument is present. For example, the instrument may be a biopsy needle. The training medical images may be comprised of image sequence subsets. Each image within an image sequence subset may be captured at different settings of the ultrasound imaging system 132 without moving a position of the probe 134. The different settings may include varying depths and corresponding frequencies (e.g., because frequency is set lower as depth is increased). For example, an image sequence subset may include a first image of a patient's anatomical structure captured at a first depth-frequency combination, a second image of the patient's anatomical structure captured at a second depth-frequency combination, a third image of the patient's anatomical structure captured at a third depth-frequency combination, and so on. The image sequence within each subset may include at least two images of a same patient's anatomical structure captured at two different depth-frequency combinations.

In some examples, the training medical images may be labeled such that supervised learning techniques may be implemented to generate and train the machine learning model at step 1104. For example, the images may include annotations that identify at least a portion of the instrument. In some examples, the portion identified may include at least a distal end of the instrument. The annotations may also indicate anatomical structures present in the images. In other examples, the training medical images may be unlabeled and unsupervised learning techniques may be implemented to train the machine learning model at step 1104. The training medical images may also undergo pre-processing (similar to the pre-processing described at step 204 of FIG. 2).

At step 1104, the machine learning model for predicting a location of an instrument may be generated and trained using the plurality of training medical images. For example, a first image sequence subset of the training medical images may be input to the machine learning model. The machine learning model may predict a location of at least a portion of the instrument included within the subset. In some examples, the prediction may include a predicted location of the distal end of the instrument. For example, the machine learning model may identify at least a portion of the instrument in the image and then determine an orientation and/or length of the instrument.

In some examples, when the training medical images are labeled and supervised learning techniques are implemented to train the machine learning model, the predicted location of the instrument output by the machine learning model for the training medical image may be compared to the label corresponding to the training medical image to determine a loss or error. For example, a predicted location of the instrument in the first image sequence subset may be compared to the known location of at least a portion of the instrument within the first image sequence subset identified by the corresponding label. The machine learning model may be modified or altered (e.g., weights and/or bias may be adjusted) based on the error to improve an accuracy of the machine learning model. This process may be repeated for each image sequence subset within the training medical images or at least until a determined loss or error is below a predefined threshold. In some examples, at least a portion of the image sequence subsets within the training images and corresponding labels may be withheld and used to further validate or test the trained machine learning model.

In other examples, when unsupervised learning techniques are implemented to train the machine learning model, for a given image sequence subset, the machine learning model may extract at least a portion of the instrument as a feature from each image within the respective image sequence subset, and identify a pattern in the subset based on the identification of the instrument as a feature (e.g., using clustering). In either the supervised or unsupervised examples, once at least a portion of the instrument is identified, a location of the distal end can be determined. In some examples, the determination of the distal end may be further facilitated by other information, such as a known length of the instrument or other images from the image sequence of the subset.

Once the machine learning model is sufficiently trained, at step 1106, the trained machine learning model may be stored for subsequent use (e.g., as one of trained machine learning models 118 stored in storage devices 114). In some examples, the trained machine learning model may be a single machine learning model that is generated and trained to predict instrument locations associated with different types of instruments (e.g., instruments having different shapes, sizes, etc.). In other examples, the exemplary method 1100 may be performed to generate and train an ensemble of machine learning models, where each model predicts an instrument location associated with a particular type of instrument (e.g., a needle). When deployed to evaluate a medical image, the ensemble of machine learning models may be run in parallel.

FIG. 12 depicts a flowchart illustrating an exemplary method 1200 for predicting a location of an instrument, according to exemplary techniques presented herein. Exemplary method 1200 (e.g., steps 1202-1208) may be performed by the system 116. Exemplary method 1200 may include one or more of the following steps.

In step 1202, a sequence of medical images subsequent to an insertion of an instrument may be received from a computing device. The sequence of medical images may be a sequence of ultrasound images, and the computing device may be the imaging computing device 136 of the ultrasound imaging system 132. For example, the ultrasound imaging system 132 may be guiding a procedure that involves the insertion of the instrument into a body of the patient to reach a target. One example procedure may be a needle biopsy procedure, where a needle is inserted to reach a target mass or lesion for biopsy. To provide a physician with visualization of the inserted instrument during the procedure, the probe 134 of the ultrasound imaging system 132 may be used to send and receive sound waves at an adjustable frequency and depth from which images may be created by the imaging computing device 136. In some examples, a long-axis approach may be performed to generate images having a long-axis (LAX) view of the instrument. The LAX view may be a longitudinal view of the instrument inserted into the body, in which a length of the instrument may be visible, for example. The sequence of medical images received at step 1202 may include at least two medical images that are created by the imaging computing device 136 from sound waves sent and received by the probe 134 at different frequencies and depths while a position of the probe 134 remains static.

In some examples, the system 116 may provide instructions to the imaging computing device 136 to cause display of an audio or visual prompt for the operator of the ultrasound imaging system 132 to capture the sequence of medical images subsequent to insertion of the instrument, and the sequence of medical images may be received responsive to the prompt. For example, the application running on the imaging computing device 136 may include an instrument locating feature for locating an instrument inserted into a body, and the instructions to cause display of the prompt may be provided and displayed via an application user interface on the display 138 of the ultrasound imaging system 132 in response to the operator selecting the instrument locating feature. In some examples, as part of the selection of the instrument locating feature, the operator may also provide additional input, such as a type of the instrument (e.g., a biopsy needle) and/or size parameters of the instrument (e.g., a length and/or diameter of the biopsy needle) that may be used in subsequent steps of the method 1200. The prompt displayed may instruct the operator of the various depth and frequency combinations at which sound waves are to be sent and received by the probe 134 to create the sequence of medical images. For example, the instructions may include a first depth and frequency at which sound waves are to be initially sent and received by the probe 134 to create a first image of the sequence, a second depth and frequency at which sound waves are to be subsequently sent and received by the probe 134 to create a second image of the sequence, and so on. The prompt may further instruct the operator to keep the probe 134 positioned in the same location as they adjust depth and frequency settings between image captures.

In other examples, the application (e.g., based on instructions from the system 116) may provide signals to the imaging computing device 136 that cause an automatic adjustment of the depth and frequency at which the sound waves are sent by the probe 134 to enable automatic capture of the sequence of medical images.

At step 1204, the sequence of medical images may be provided as input to a trained machine learning model for predicting a location of the instrument, such as the trained machine learning model trained using method 1100 described with reference to FIG. 11. In examples where the exemplary method 1100 is used to generate and train an ensemble of machine learning models, the medical image may be provided as input to each machine learning model of the ensemble of machine learning models running in parallel. In some examples, when the type of instrument is indicated by the physician as part of the instrument locating feature selection, only the machine learning model trained to identify the particular type of instrument may be run. Additionally, any size parameters of the instrument input by the operator as part of the instrument locating feature selection may be provided as further input to the trained machined learning system.

At step 1206, a predicted location may be received as output from the trained machine learning model. The predicted location may include at least a distal end of the instrument. The predicted location may also include an orientation and/or length of the instrument. For example, the machine learning model may identify at least a portion of the instrument in the image and then determine an orientation and/or length of the instrument. In some examples, the predicted location output from the trained machine learning model may be subsequently provided as input to another process, such as a process for predicting a trajectory of the instrument described in detail with reference to FIGS. 13 and 14 below.

At step 1208, a visualization of the predicted location of the instrument may be provided to the computing device for display. For example, the visualization may be generated based on the prediction at post-processing step 206 described with reference to FIG. 2 and provided for display via the application executing on the imaging computing device 136. The visualization may show the predicted location of at least the distal end of the instrument relative to anatomical structures to allow the physician to confirm that no unintended contact is occurring between the instrument and the anatomical structures.

In some examples, the visualization may include at least two medical images depicting orthogonal views of the instrument simultaneously. For example, the first image may be a LAX view of the instrument in which a length of the instrument may be visible, where the first image may be one of the images from the sequence of images received (e.g., an image at a given depth and frequency that is more easily viewable by the human eye). The second image may be a short-axis (SAX) view of the instrument orthogonal to the LAX view such that only a distal end of the instrument is visible. The SAX view may be captured at the same time by the same probe as the LAX view if the probe is capable of biplane imaging and/or a different probe of the ultrasound imaging system 132 at the same time as the LAX view. In each image, the predicted location of the instrument, and particularly the predicted location of the distal end of the instrument may be visually indicated. An example application user interface displaying a visualization having two medical images depicting orthogonal views of the instrument is shown in FIG. 15 below.

In other examples, the visualization may include a three-dimensional (3D) representation of the anatomical structure. The 3D representation may be generated from the sequence of medical images. Additionally, the predicted location of the instrument output by the trained machine learning model may be utilized as part of the generation process such that the 3D representation visually indicates the predicted location of the instrument, and particularly the distal end of the instrument.

In some examples, the exemplary method 1200 may be repeated as the instrument is inserted further into the body to continue to track at least the distal end of the instrument as the instrument is moved.

As described above with reference to FIGS. 11-12, the trained machine learning model may be trained to receive a sequence of medical images captured at different depths and frequencies from which the location of the instrument is predicted. For example, if the probe 134 is not aligned with a long axis of the instrument for a given image captured, the model may only learn/predict a location of a cross-section of the instrument at the given depth/frequency at which the image was captured. Therefore, multiple medical images at different depths and frequencies may be needed to enable an entire length of the instrument to be learned and predicted by the trained machine learning model.

In other aspects, a machine learning model may be trained to predict the location of the instrument using one medical image (e.g., if the medical image is captured when probe 134 is substantially aligned with a long axis of the instrument). Additionally, if the probe 134 is not substantially aligned with the long axis of the instrument in the medical image currently captured, a prompt may be provided to the operator to adjust a position and/or orientation of the probe to capture an image having a better viewing angle of the instrument (e.g., a viewing angle showing the long axis of the instrument). For example, a determination of whether the image of the instrument is optimal and a subsequent determination of a suggested direction for moving the probe when the image is not optimal may be determined using a similar process described above with reference to FIGS. 8-9. Once the medical image having the better viewing angle of the instrument is captured, the medical image may be provided as input to the machine learning model trained to predict the location of the instrument using the one medical image.

FIG. 13 depicts a flowchart illustrating an exemplary method 1300 for training a machine learning model (e.g., one of trained machine learning models 118) to predict instrument trajectory, according to exemplary techniques presented herein. Exemplary method 1300 (e.g., steps 1002-1006) may be performed by system 116. Exemplary method 1300 may include one or more of the following steps.

At step 1302, a plurality of labeled training medical images that each include an instrument and a target for the instrument may be received (e.g., from the medical imaging databases 160 over the network 120). For example, a training medical image may be an ultrasound image of an anatomical structure of a patient that includes an instrument at a given location following insertion of the instrument into the patient and a target of the instrument associated with the anatomical structure. The training medical images may be labeled with annotations that identify the anatomical structure, the instrument, the target, an angle of entry of the instrument inserted (e.g., an insertion angle), a location of at least the distal end of the instrument that is approaching the target, and/or a location of the target. Additionally, each of the training medical images may have a corresponding ground truth label that indicates a known trajectory of the instrument from the distal end of the instrument to the target.

The training medical images may undergo pre-processing (similar to the pre-processing described at step 204 of FIG. 2). In some examples, as part of the pre-processing, the annotations may be extracted or otherwise identified from the training medical images to form labels separate from the training medical images. In other examples, the annotations may be received as labels separate from the training medical images.

At step 1304, a machine learning model for predicting instrument trajectory may be generated and trained using the plurality of labeled training medical images. For example, a training medical image including an instrument and a target for the instrument may be input to the machine learning model. The machine learning model may predict a trajectory of the instrument from a distal end of the instrument to the target. To train the machine learning model, the trajectory output by the machine learning model for the training medical image may be compared to the ground truth label corresponding to the training medical image to determine a loss or error. For example, a predicted trajectory for a first medical training image may be compared to the known trajectory of the instrument from the distal end of the instrument to the target identified by the corresponding ground truth label for the first training medical image. The machine learning model may be modified or altered (e.g., weights and/or bias may be adjusted) based on the error to improve an accuracy of the machine learning model. This process may be repeated for each training medical image or at least until a determined loss or error is below a predefined threshold. In some examples, at least a portion of the training medical images and corresponding labels may be withheld and used to further validate or test the trained machine learning model Once the machine learning model is sufficiently trained, at step 1306, the trained machine learning model may be stored for subsequent use (e.g., as one of trained machine learning models 118 stored in storage devices 114). In some examples, the trained machine learning model may be a single machine learning model that is generated and trained to predict instrument trajectories associated with different types of instruments (e.g., instruments having different shapes, sizes, etc.). In other examples, the exemplary method 1300 may be performed to generate and train an ensemble of machine learning models, where each model predicts an instrument trajectory associated with a particular type of instrument (e.g., a needle). When deployed to evaluate a medical image, the ensemble of machine learning models may be run in parallel.

FIG. 14 depicts a flowchart illustrating an exemplary method for predicting instrument trajectory, according to exemplary techniques presented herein. Exemplary method 1400 (e.g., steps 1402-1412) may be performed by the system 116. Exemplary method 1400 may include one or more of the following steps.

At step 1402, a sequence of medical images including an inserted instrument and a target of the instrument may be received from a computing device. The computing device may be the imaging computing device 136 of the ultrasound imaging system 132. The ultrasound imaging system 132 may be guiding a procedure that involves the insertion of the instrument into a body of the patient to reach the target, such as a needle biopsy procedure where a needle is inserted to reach a target mass or lesion for biopsy. To provide a physician with visualization of the inserted instrument during the procedure, the probe 134 may be used to send and receive sound waves at an adjustable frequency and depth from which images may be created by the imaging computing device 136. In some examples, a long-axis approach may be performed to generate images having a LAX view of the instrument, as described above in more detail with reference to FIG. 12. The sequence of medical images received at step 1402 may include at least two medical images that are created by the imaging computing device 136 from sound waves sent and received by the probe 134 at different depths and frequencies while a location or positioning of the probe 134 remains static.

As described in detail with reference to step 1202 of method 1200, in some examples, the sequence of medical images may be received responsive to a prompt that is provided to the operator via the application user interface to capture each image of the sequence at the varying depth-frequency combinations. The prompt may be displayed upon a selection of an instrument locating feature selection, which may also cause the operator to provide additional input, such as a type of the instrument (e.g., a biopsy needle) and/or size parameters of the instrument (e.g., a length and/or diameter of the biopsy needle) that may be used in subsequent steps of the method 1400. In other examples, the application (e.g., based on instructions from the system 116) may provide signals to the imaging computing device 136 that cause an automatic adjustment of the depth and frequency at which the sound waves are sent by the probe 134 to enable automatic capture of the sequence of medical images.

At step 1404, the sequence of medical images may be provided as input to a first trained machine learning model to obtain a predicted location of the instrument. The predicted location of the instrument may include at least a distal end of the instrument. The first trained machine learning model may be a machine learning model trained and used for predicting instrument location described with reference to FIGS. 12 and 13.

At step 1406, an insertion angle of the instrument may be determined based on a location of insertion of the instrument and the predicted location of the instrument (particularly the distal end of the instrument). The location of the insertion of the instrument may be extracted from the sequence of medical images. In some examples, the operator as part of the tracking features selection may also input a location of the insertion of the instrument.

At step 1408, the sequence of medical images, the predicted location of the instrument, and the insertion angle of the instrument may be provided as input to a second trained machine learning model for predicting instrument trajectory. Optionally, any size parameters of the instrument provided as part of the instrument locating feature selection may also be provided as input. The second trained machine learning model may be the trained machine learning model trained using method 1300 described with reference to FIG. 13. In examples where the exemplary method 1300 is used to generate and train an ensemble of machine learning models, the medical image may be provided as input to each machine learning model of the ensemble of machine learning models running in parallel. In some examples, when the type of instrument is indicated as part of the instrument locating feature selection, only the machine learning model trained to identify the particular type of instrument may be run.

At step 1410, a predicted trajectory of the instrument to reach the target may be received as output of the second trained machine learning model. For example, the predicted trajectory may be a path from the distal end of the instrument to the target. At step 1412, a visualization of the predicted trajectory may be provided to the computing device for display. For example, the visualization may be generated based on the prediction at post-processing step 206 described with reference to FIG. 2 and provided for display (e.g., on display 138) via the application executing on the imaging computing device 136.

In some examples, the visualization may include at least two medical images depicting orthogonal views of the instrument simultaneously. For example, the first image may be a LAX view of the instrument in which a length of the instrument may be visible, where the first image may be one of the images from the sequence of medical images received. In some examples, the image selected from the sequence may be the image at a given depth and frequency that is most easily viewable by the human eye. The second image may be a short-axis (SAX) view of the instrument orthogonal to the LAX view such that only a distal end of the instrument is visible. The SAX view may be captured at the same time by the same probe as the LAX view if the probe is capable of biplane imaging and/or a different probe at the same time as the LAX view. In at least the first image comprising the LAX view, the predicted trajectory of the instrument is visually. Additionally, in each of the first and second images, the predicted location of the instrument, and particularly the predicted location of the distal end of the instrument may be visually indicated. An example application user interface displaying a visualization having two medical images depicting orthogonal views of the instrument is shown in FIG. 15 below.

In other examples, the visualization may include a three-dimensional (3D) representation of the anatomical structure. The 3D representation may be generated from the sequence of medical images. Additionally, the predicted trajectory of the instrument and/or the predicted location of the instrument output by the trained machine learning model may be utilized as part of the generation process such that the 3D representation visually indicates the predicted trajectory of the instrument to reach the target and/or the predicted location of the instrument, and particularly the distal end of the instrument.

The exemplary method 1400 may be repeated as the operator moves the probe 134 to enable continuous visualization of the location of the instrument and the trajectory of the instrument to reach the target throughout the procedure.

The examples described above in FIGS. 13 and 14 include training and implementation of a second machine learning model for predicting instrument trajectory that is separate from a first machine learning model for predicting instrument location, such as the model described in FIGS. 11 and 12. In other examples, rather than train and implement the second machine learning model for predicting instrument trajectory, the system 116 may computationally determine and visually project the instrument trajectory based on the predicted instrument location by the first machine learning model for predicting instrument location (e.g., based on the determined orientation and/or length of the instrument and insertion angle).

FIG. 15 is an example application user interface 1500 displaying a predicted instrument location and trajectory. For example, during a procedure, such as a needle biopsy procedure, the application user interface 1500 may be presented on the display 138 via the application associated with the system 116 that is running on the imaging computing device 136 of the ultrasound imaging system 132. The user interface 1500 may simultaneously display images 1502, 1504 with orthogonal views of an instrument 1506, such as the needle. For example, a first image 1502 may be a LAX view of the instrument 1506 and a second image 1504 may be a SAX view of the instrument 1506 orthogonal to the LAX view such that only a distal end 1508 of the instrument 1506 is visible. In each of the first and second images 1502, 1504, a location of the distal end 1508 of the instrument predicted using the exemplary method 1100 described with reference to FIG. 11 may be visually indicated. For example, the distal end 1508 may be highlighted, shaded, or colored to distinguish the distal end 1508 from a remaining portion of the instrument 1506.

Additionally, as shown in the first image 1502, a target 1510 of the instrument (e.g., a mass for the needle to biopsy) and a predicted trajectory 1512 for the instrument (e.g., from the distal end 1508) to the target 1510 may also be displayed. The predicted trajectory 1512 may be determined and provided based on the exemplary method 1300 described with reference to FIG. 13.

Further, the user interface 1500 may include probe direction indicators 1514 that suggest a direction for moving the probe 134 of the ultrasound imaging system 132 to, e.g., capture a more optimal image of the instrument 1506, and particularly a distal end 1508 of the instrument 1506. The probe direction indicators 1514 may include arrows that indicate for an operator to slide the probe (e.g., forward, backward, right, or left) and/or rotate the probe. The probe direction indicators 1514 may be animated such that an arrow pointing in the direction of the suggested movement may be highlighted, flashed, or otherwise visually brought to the attention of the operator. A determination of whether the image of the instrument is optimal and a subsequent determination of a suggested direction for moving the probe when the image is not optimal may be determined using a similar process described above with reference to FIGS. 8-9.

Diagnostic and Interventional Observations: Anatomical Feature Identification, Visualization, and Probe-Anatomical Feature Alignment Techniques presented in FIGS. 16-17 describe the training and use of a machine learning model that enables real-time identification and visualization of anatomical features labeled within ultrasound images displayed by an ultrasound imaging system 132 (e.g., vis the display 138). Additionally, upon identification and visualization of an anatomical feature of interest, the anatomical feature may be marked to provide context-aware imaging to the operator as a probe 134 of the ultrasound imaging system 132 is moved. Techniques presented in FIGS. 18-19 describe another machine learning model that is trained and used to detect probe alignment with an anatomical feature that is identified, e.g., as output of the machine learning model described with reference to FIGS. 16-17.

To provide an illustrative example, as an operator of the ultrasound imaging system 132 moves the probe along a median nerve into the carpal tunnel, secondary to changes in depth within the carpal tunnel, it becomes difficult for the human eye to visualize at the distal tunnel as it branches into smaller nerves. Certain image-guided procedures to treat carpal tunnel syndrome, for example, may involve the insertion of a sharp tool, such as a knife, in this area of the patient's body. Real-time recognition and visual labeling of the anatomical features present (e.g., veins, artery, nerves, tendon, ligament, cartilage, muscle, bone, and the like) within the images displayed to guide the procedure, may increase the confidence of the physician that the knife is being inserted relative to a desired anatomical feature (and not an unintended anatomical feature).

FIG. 16 depicts a flowchart illustrating an exemplary method 1600 for training a machine learning model (e.g., one of trained machine learning models 118) to identify anatomical features, according to exemplary techniques presented herein. Exemplary method 1300 (e.g., steps 1602-1606) may be performed by the system 116. Exemplary method 1600 may include one or more of the following steps.

At step 1602, a plurality of training medical images may be received (e.g., from medical imaging databases 160 over the network 120). The training medical images may include ultrasound images of an anatomical structure having a plurality of anatomical features. For example, the ultrasound images may be of a wrist, and the anatomical features may include bone, nerve, ligament, and/or tendon (e.g., dependent on a view of the images). In some examples, the annotations for the anatomical features may be broader categories of anatomical features, such as vein, artery, vessel, bone, nerve, ligament, tendon, cartilage, etc., rather than the specific anatomical feature for that structure. In other words, continuing with the example where the image is of the wrist, the image may be annotated with nerve rather than median nerve and artery rather than ulnar artery. Training medical images may be received for a plurality of different types of anatomical structures (e.g., wrists, knee joints, shoulder joints, etc.).

The training medical images may undergo pre-processing (similar to the pre-processing described at step 204 of FIG. 2). In some examples, as part of the pre-processing, the annotations may be extracted as features from or otherwise removed from the training medical images and stored separately as ground truth labels for use in training a machine learning model at step 804. Alternatively, the annotations may be received separately from but with correspondence to the training medical training images.

At step 1604, the machine learning model for identifying the plurality of anatomical features in a target image of the anatomical structure may be generated and trained using the plurality of training medical images. For example, a training medical image of the anatomical structure may be input to the machine learning model. The machine learning model may output, as a prediction, anatomical features of the anatomical structure.

To train the machine learning model, the anatomical features output by the machine learning model for the training medical image may be compared to the ground truth label corresponding to the training medical image (e.g., the annotations of the anatomical features) to determine a loss or error. For example, anatomical features identified within a first training image of the anatomical structure may be compared to the known anatomical features within the first training image of the anatomical structure indicated by the annotations within the corresponding ground truth label. The machine learning model may be modified or altered (e.g., weights and/or bias may be adjusted) based on the error to improve an accuracy of the machine learning model. This process may be repeated for each training image or at least until a determined loss or error is below a predefined threshold. In some examples, at least a portion of the training images and corresponding labels may be withheld and used to further validate or test the trained machine learning model.

Once the machine learning model is sufficiently trained, at step 1606, the trained machine learning model may be stored for subsequent use (e.g., as one of trained machine learning models 118 stored in storage devices 114). In some examples, the trained machine learning model may be a single machine learning model that is generated and trained to identify anatomical structures in a plurality of different anatomical structures. In other examples, the exemplary method 1600 may be performed to generate and train an ensemble of machine learning models, where each model identifies anatomical features of a particular anatomical structure (e.g., one model may identify anatomical features of a shoulder joint, another model may identify anatomical features of a wrist, a further model may identify anatomical features of a knee joint, and so on.) When deployed to evaluate a medical image, the ensemble of machine learning models may be run in parallel.

FIG. 17 depicts a flowchart illustrating an exemplary method 1700 for visualizing anatomical features of an anatomical structure identified in a medical image, according to exemplary techniques presented herein. Exemplary method 1700 (e.g., steps 1702-1708) may be performed by the system 116. Exemplary method 1700 may include one or more of the following steps.

At step 1702, a medical image of an anatomical structure (e.g., a target image) may be received from a computing device. The computing device may be the imaging computing device 136 of the ultrasound imaging system 132. The ultrasound imaging system 132 may be facilitating a diagnosis of a patient during an examination and/or guiding an intervention. The medical image may be generated by the imaging computing device 136 from the sound waves sent and received from the probe 134 and received in real-time, e.g., via the application associated with the system 116 running on the imaging computing device 136. In some examples, an operator may also input, via the application user interface, a type of anatomical structure being imaged (e.g., a wrist, a shoulder joint, a knee joint, etc.).

At step 1704, the medical image may be provided as input to a trained machine learning model for identifying anatomical features of the anatomical structure, such as a trained anatomical feature identification machine learning model trained using method 1600 described with reference to FIG. 16. In examples where the exemplary method 1600 is used to generate and train an ensemble of machine learning models, the medical image may be provided as input to each machine learning model of the ensemble of machine learning models running in parallel. In some examples, when the type of anatomical structure is selected by the physician, only the machine learning model trained to identify anatomical features of the type of anatomical structure selected is run (e.g., to conserve computational resources).

At step 1706, anatomical features identified in the medical image may be received as output (e.g., as a prediction) from the trained machine learning model. Based on a level of specificity of the annotations used to train the machine learning model, the anatomical features identified may be broad categories of anatomical features (e.g., nerve, artery, bone) or may be specific anatomical features of the given anatomical structure (e.g., median nerve, ulnar artery, pisiform carpal bone).

Figure 18:
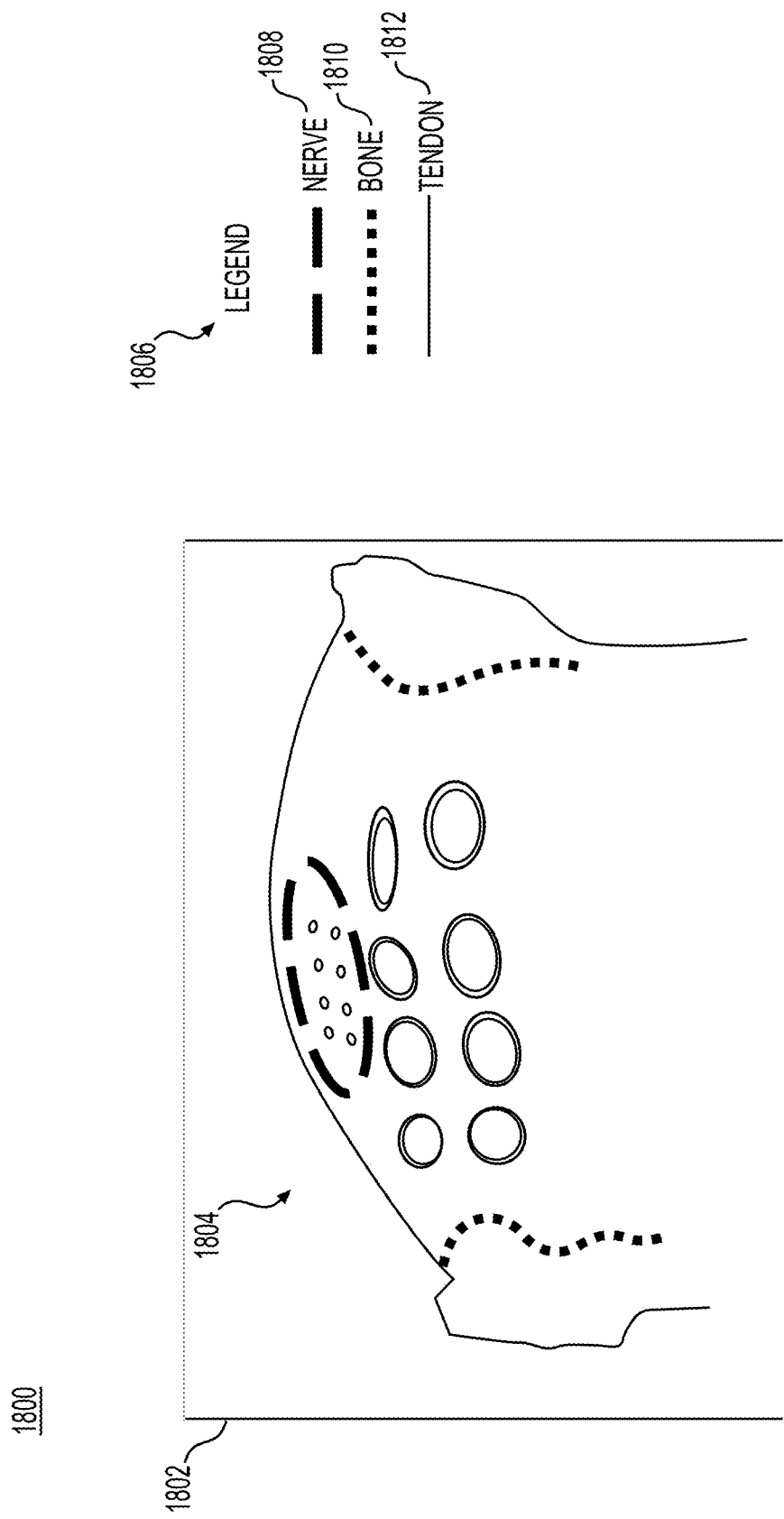
FIG. 18 illustrates an example application user interface displaying a visualization of anatomical features of an anatomical structure identified within a medical image of the anatomical structure, according to techniques described herein.

At step 1708, a visualization of the anatomical features identified within the medical image may be provided to the computing device for display. For example, the visualization may be generated based on the prediction at post-processing step 206 described with reference to FIG. 2. In some examples, within the visualization, the anatomical features identified may be labeled or distinguished from one another using a visual scheme. For example, different colors, shading, patterning and/or highlighting may be used for each of categories of anatomical features. For example, a first color may be used to identify bone, a second color may be used to identify nerve, a third color may be used to identify tendon, and so on. An example application user interface displaying the visualization is shown in FIG. 18 below. The anatomical features may be labeled in all axes.

In some examples, the anatomical features of the anatomical structure identified and output by the trained machine learning model may be provided as input into another process. One example process may include a process for detecting probe alignment with one or more of the identified anatomical features, as described with reference to FIGS. 19 and 20 below. Another example process may facilitate context-aware imaging. For example, one or more anatomical features identified in the medical image may be marked for continued viewing as the operator moves the probe and captures subsequent images of the anatomical structure. In some examples, the operator may provide input, e.g., via the application, to indicate which of the anatomical features are to be marked for continued viewing. For example, the operator may provide touch input to the display of the computing device in an area of the medical image corresponding to the anatomical features to be marked. A position of the respective anatomical features marked for continued viewing relative to the probe location associated with the medical image may be identified for use as a reference.

The location of the anatomical structures themselves are static. That is, only the probe is moving, not the anatomical structure within the patient's body. Therefore, by knowing a first position of the anatomical feature relative to the probe prior to the probe's motion (e.g., the reference) and determining a motion of the probe, a second position of the anatomical feature relative to the probe's motion may be determined. The motion of the probe may be detected using sensors attached to the probe, such as accelerometers, gyroscopes, and/or inertial sensors. Once determined, the second position of the anatomical feature may be visually indicated within a corresponding medical image generated upon the movement of the probe.

FIG. 18 is an example application user interface 1800 displaying a visualization 1804 of anatomical features of an anatomical structure identified within a medical image 1802 of the anatomical structure. Application user interface 1800 may be a user interface of the application associated with the system 116 that is executing on a computing device, such as the imaging computing device 136 of the ultrasound imaging system 132. As the ultrasound imaging system 132 is operating to image the anatomical structure of the patient, the application user interface 1800 may be displayed on the display 138 such that an operator (e.g., a physician) may view the visualization 1804 while continuing to image the patient. In this illustrative example, the anatomical structure being imaged may be a wrist of the patient.

Within the visualization 1804, the anatomical features of the wrist identified within the medical image 1802 (e.g., via method 1700 described above with reference to FIG. 17) may be labeled or distinguished from one another using a visual scheme. The application user interface 1800 may include a legend 1806 or other similar key to inform the physician viewing the image of the visual scheme used to label each of the identified anatomical features. For example, anatomical features of the wrist identified within the medical image 1802 may include nerve 1808, bone 1810, and tendon 1812, among other examples, and each category of anatomical feature may be labeled with a different outlining scheme within the medical image 1802. For example, as shown in the legend a first outline pattern may be used to identify nerve 1808, a second outline pattern may be used to identify bone 1810, and a third outline pattern may be used to identify tendon 1812 within the medical image 1802. In other examples, rather than patterning, the visual scheme may be based on color, shading, highlighting and/or other similar visual schemes.

The application user interface 1800 described above is provided merely as an example, and may include additional, fewer, different, or differently arranged information and/or visual schemes than depicted in FIG. 18.

FIG. 19 depicts a flowchart illustrating an exemplary method 1900 for training a machine learning model (e.g., one of trained machine learning models 118) to detect probe alignment with an anatomical feature identified within a medical image, according to exemplary techniques presented herein. Exemplary method 1900 (e.g., steps 1902-1906) may be performed by the system 116. Exemplary method 1600 may include one or more of the following steps.

At step 1902, a plurality of labeled training medical images may be received (e.g., from medical imaging databases 160 over the network 120). The training medical images may include ultrasound images of an anatomical structure having a plurality of anatomical features, each of the ultrasound images having been generated by an ultrasound imaging system similar to ultrasound imaging system 132. In some examples, the training medical images may be representative of a plurality of different anatomical structures. The training medical images may include annotations for at least one or more anatomical features of interest, such as anatomical features for which the probe of an ultrasound imaging system is to be in alignment with to achieve an optimal image. As one illustrative example, for an optimal image, the probe may be in a parallel alignment with tendon or ligament fibers of a joint, referred to herein generally as fibers. A sagittal cross-sectional area of a fiber (e.g., going from the cross-section down the fiber obliquely) decreases as the probe approaches parallel (e.g., in-line) alignment with the fiber. In contrast, as the probe moves away from in-line alignment, the sagittal cross-sectional area of the fiber increases again. Additionally, the training medical images may have corresponding ground truth labels that indicate whether the one or more anatomical features are in sufficient alignment with the probe or not. In some examples, the corresponding ground truth labels may also include orientation details associated with the probe that resulted in the given alignment.

The training medical images may undergo pre-processing (similar to the pre-processing described at step 204 of FIG. 2). In some examples, as part of the pre-processing, the annotations may be extracted or otherwise identified from the training medical images to form labels separate from the training medical images. In other examples, the annotations may be received as labels separate from the training medical images.

At step 1904, a machine learning model for detecting whether there is probe-anatomical feature alignment may be generated and trained using the plurality of labeled training medical images. For example, a training medical image of the anatomical structure may be input to the machine learning model. The machine learning model may output, as a prediction, whether the probe is in sufficient alignment with the one or more anatomical features of interest. For example, the output may be either a prediction that there is sufficient alignment or a prediction that there is insufficient alignment. In some examples, the output may also include a predicted orientation of the probe resulting in the alignment.

To train the machine learning model, the alignment prediction output by the machine learning model for the training medical image may be compared to the ground truth label corresponding to the training medical image to determine a loss or error. For example, an alignment prediction for a first training medical image may be compared to the known sufficiency or insufficiency of the probe's alignment with the one or more anatomical features of interest identified by the corresponding ground truth label. Additionally, when the alignment prediction output also includes the predicted orientation of the probe resulting in the alignment, the predicted orientation may be compared to the known orientation of the probe included in the corresponding ground truth label. The machine learning model may be modified or altered (e.g., weights and/or bias may be adjusted) based on the error to improve an accuracy of the machine learning model. This process may be repeated for each training image or at least until a determined loss or error is below a predefined threshold. In some examples, at least a portion of the training images and corresponding labels may be withheld and used to further validate or test the trained machine learning model.

Once the machine learning model is sufficiently trained, at step 1906, the trained machine learning model may be stored for subsequent use (e.g., as one of trained machine learning models 118 stored in storage devices 114). In some examples, the trained machine learning model may be a single machine learning model that is generated and trained to predict probe-anatomical feature alignment for a plurality of different anatomical structures. In other examples, the exemplary method 1900 may be performed to generate and train an ensemble of machine learning models, where each model predicts whether there is an alignment of the probe and anatomical feature(s) of interest for a particular anatomical structure given anatomical structure (e.g., one model to detect probe-anatomical feature alignment for a shoulder joint, another to identify probe-anatomical feature alignment for a wrist, and so on). When deployed to evaluate a medical image of the anatomical structure, the ensemble of machine learning models may be run in parallel.

FIG. 20 a flowchart illustrating an exemplary method 2000 for detecting probe alignment with one or more anatomical features of an anatomical structure identified within a medical image of the anatomical structure, according to exemplary techniques presented herein. Exemplary method 2000 (e.g., steps 2002-2010) may be performed by the system 116. Exemplary method 2000 may include one or more of the following steps.

At step 2002, a medical image of an anatomical structure (e.g., a target image) may be received from a computing device. The computing device may be the imaging computing device 136 of the ultrasound imaging system 132. The ultrasound imaging system 132 may be facilitating a diagnosis of a patient during an examination and/or guiding an intervention. The medical image may be generated by the imaging computing device 136 from the sound waves sent and received from the probe 134 and received in real-time, e.g., via the application associated with the system 116 running on the imaging computing device 136. In some examples, an operator may also input, via the application user interface, a type of anatomical structure being imaged (e.g., a wrist, a shoulder joint, a knee joint, etc.)

At step 2004, the medical image may be provided as input to a first trained machine learning model to obtain, as output of the first trained machine learning model, anatomical features identified in the medical image. The first trained machine learning model may be the trained machine learning model for identifying anatomical features of the anatomical structure described with reference to FIGS. 16 and 17.

At step 2006, the medical image annotated with the identified anatomical features output by the first trained machine learning model may be provided as input to a second trained machine learning model for predicting whether there is probe-anatomical feature alignment. That is, the second trained machine learning model may predict whether the probe 134 capturing the medical image is in alignment with one or more anatomical features of interest for the anatomical structure. The second trained machine learning model may be the trained machine learning model trained using method 1900 described with reference to FIG. 19. In examples where the exemplary method 1900 is used to generate and train an ensemble of machine learning models, the medical image may be provided as input to each machine learning model of the ensemble of machine learning models running in parallel. In some examples, when the type of anatomical structure is selected by the physician, only the machine learning model trained to predict probe-anatomical feature alignment associated with the type of anatomical structure (e.g., trained based on the specific anatomical feature(s) of interest for that type of anatomical structure) may be run (e.g., to conserve computing resources).

In some examples, the medical image may be annotated with all identified anatomical features output by the first trained machine learning model prior to being input to the second trained machine learning model. In other examples, the medical image received may only be annotated with the specific anatomical feature(s) (e.g., from the identified anatomical features) that are of interest for the given anatomical structure.

At step 2008, an alignment prediction may be received as output of the second trained machine learning model. The alignment prediction may include whether the probe is sufficiently aligned or is insufficiently aligned with the anatomical feature(s) of interest for the anatomical structure. Additionally, the alignment prediction may include a predicted orientation of the probe resulting in the alignment or misalignment.

At step 2010, an indication of the alignment prediction may be provided to the computing device for display (e.g., via the application executing on imaging computing device 136). For example, a visualization may be generated based on the alignment prediction at post-processing step 206 described with reference to FIG. 2. As one example, if the prediction is that the probe is sufficiently aligned with the anatomical feature(s) of interest for the anatomical structure, a positive alignment indicator may be overlaid on the medical image to notify the operator that the probe is in alignment and thus, the optimal image is being captured. As another example, if the prediction is that the probe is insufficiently aligned with the anatomical feature(s) of interest for the anatomical structure, a negative alignment indicator may be overlaid on the medical image to notify the operator that the probe is not in alignment and thus, other, more optimal images should be captured. The alignment indicators may include text, graphics, animation, and/or a combination thereof.

In some examples, when the probe is insufficiently aligned and the alignment prediction further includes the predicted orientation of the probe resulting in the misalignment, directional instructions may be generated to guide the operator to adjust a current orientation of the probe corresponding to the predicted orientation in order to achieve alignment and an optimal image capture. For example, as part of the training, the second trained machine learning model may learn a probe orientation associated with probe-anatomical feature alignment from the labeled training medical images. Accordingly, the learned probe orientation associated with probe-anatomical feature alignment may be compared to current probe orientation to generate directional instructions to adjust the current probe orientation to the learned probe orientation. In some examples, the directional instructions may be in the form of probe direction indicators similar to the probe direction indicators discussed above with reference to FIGS. 10 and 15. The exemplary method 2000 may then be iteratively repeated as the probe is reoriented (e.g., is adjusted responsive to the directional instructions).

To provide an illustrative example of an operator's experience while the method 2000 is repeatedly being performed, the operator may place the probe 134 in contact with the patient's skin in a first orientation, second orientation, third orientation, etc. (e.g., as part of a scanning motion). As a medical image is captured at each orientation and is processed to predict a probe-anatomical feature alignment (e.g., via the steps of method 2000), an alignment indicator and/or directional instructions may be displayed on the display 138. Returning to the illustrative example where the probe may be in a parallel alignment with fibers of a joint to obtain an optimal image, a sagittal cross-sectional area of a fiber decreases as the probe approaches parallel (e.g., in-line) alignment with the fiber and increases again as the probe moves away from the in-line alignment. Continuing with this example, when the probe is in the first orientation, the operator may be instructed to reorient the probe to the second orientation based on a predicted misalignment. Given the misalignment, the sagittal cross-sectional area of the fiber has a first area within the medical image corresponding to the first orientation. When in the second orientation, the operator may be instructed to reorient the probe to the third orientation (e.g., an orientation between the first and the second orientation) based on a predicted misalignment in an opposite direction. For example, given the misalignment, the sagittal cross-sectional area of the fiber has a second area within the medical image corresponding to the second orientation, and the second area may be larger than the first area within the medical image corresponding to the first orientation indicating that the operator's reorientation overshot the alignment during the scan.

Diagnostic and Interventional Observations: Optimal Image Capture Determinations FIG. 21 depicts a flowchart illustrating an exemplary method 2100 for training a machine learning model (e.g., one of trained machine learning models 118) to identify an optimal image frame, according to exemplary techniques presented herein. Exemplary method 2100 (e.g., steps 2102-2106) may be performed by the system 116. Exemplary method 2100 may include one or more of the following steps.

At step 2102, a plurality of labeled training medical images of an anatomical structure affected by a musculoskeletal disorder may be received. The training medical images may be comprised of a plurality of image subsets corresponding to a minimum number of image types to be obtained as part of a procedure associated with the musculoskeletal disorder. For example, each image within an image subset corresponds to an image type to be obtained as part of the procedure. In some examples, the procedure may be a diagnosing procedure or a treatment procedure. The image types to be obtained may include particular viewing angles of anatomical features within the anatomical structure. As one illustrative example, the procedure may be a diagnosing procedure for carpal tunnel syndrome in which at least three images of the wrist are to be obtained from a first viewing angle, a second viewing angle, and a third viewing angle. In some examples, the training medical images may represent a plurality of different procedures associated with a plurality of different types of musculoskeletal disorders.

The training medical images may be annotated with anatomical features of the anatomical structure, including at least any anatomical features that are to be included within one or more of the image types. The training medical images may also have corresponding ground truth labels. For example, each image within an image subset may be labeled an optimal image or a non-optimal image for the respective image type. In some techniques, the ground truth labels may also include an orientation of the probe (e.g., affecting a viewing angle captured) resulting in the optimal or not optimal image. The training medical images may undergo pre-processing (similar to the pre-processing described at step 204 of FIG. 2). In some examples, as part of the pre-processing, the annotations may be extracted or otherwise identified from the training medical images to form labels separate from the training medical images. In other examples, the annotations may be received as labels separate from the training medical images.

At step 2104, a machine learning model for predicting an optimal image for each image type may be generated using the plurality of labeled training medical images. To train the machine learning model, the prediction output by the machine learning model for the training medical image may be compared to the ground truth label corresponding to the training medical image to determine a loss or error. For example, a prediction of optimal or not optimal for a first training medical image of a first image subset corresponding to a first image type may be compared to the corresponding ground truth label for the training medical image as being optimal or not. Additionally, when the prediction output also includes the predicted orientation of the probe resulting in the optimal or not optimal image, the predicted orientation may be compared to the known orientation of the probe included in the corresponding ground truth label. The machine learning model may be modified or altered (e.g., weights and/or bias may be adjusted) based on the error to improve an accuracy of the machine learning model. This process may be repeated for each training image or at least until a determined loss or error is below a predefined threshold. In some examples, at least a portion of the training images and corresponding labels may be withheld and used to further validate or test the trained machine learning model.

Once the machine learning model is sufficiently trained, at step 2106, the trained machine learning model may be stored for subsequent use e.g., as one of trained machine learning models 118 stored in storage devices 114). In some examples, the trained machine learning model may be a single machine learning model that is generated and trained to predict an optimal image for each image type to be obtained for a plurality of different procedures associated with a plurality of different musculoskeletal disorders. In other examples, the exemplary method 2100 may be performed to generate and train an ensemble of machine learning models, where each model predicts an optimal image for each image type to be obtained for a particular procedure associated with a particular musculoskeletal disorder (e.g., one model may predict an optimal image for each image type to be obtained for diagnosing carpal tunnel, another may detect an optimal image for each image type to be obtained during a needle biopsy of an area of interest on a shoulder joint, and so on). When deployed to evaluate a medical image of the anatomical structure, the ensemble of machine learning models may be run in parallel FIG. 22 depicts a flowchart illustrating an exemplary method 2200 for capturing an optimal image frame, according to exemplary techniques presented herein. Exemplary method 2200 (e.g., steps 2202-2210) may be performed by the system. Exemplary method 2200 may include one or more of the following steps.

At step 2202, a type of procedure being performed may be received from a computing device. The computing device may include the imaging computing device 136 of the ultrasound imaging system 132 on which the application associated with the system 116 is executing. A user of the computing device may select, via a user interface of the application, the type of procedure. In some examples, upon receiving the selection of the type of the procedure, the application may provide instructions to an operator indicating the minimum set of image types to be obtained for the selected type of the procedure. Additionally, the application may provide instructions prompting the operator to place the probe 134 in contact with the patient's skin and orient the probe 134 to capture a medical image of a respective image type (e.g., the respective image type being one image type in the minimum set of image types). At step 2204, the medical image of the respective image type may be received from a computing device (e.g., is a live image received in real-time).

At step 2206, the medical image of the respective image type may be provided as input to a trained machine learning model, such as the trained machine learning model trained using method 2100 described with reference to FIG. 21. In some examples, an ensemble of machine learning models for predicting an optimal image for each image type to be obtained for a plurality of different procedures associated with a plurality of different musculoskeletal disorders may be generated, trained, and stored (e.g., as disclosed in the method 2100) in e.g., storage device 114. In such examples, the system 116 may query the storage device 114 for the type of procedure received at step 2202 to obtain the corresponding trained machine learning model for predicting the optimal image for each image type (e.g., including the respective image type) to be obtained for the type of procedure.

At step 2208, a prediction of whether the medical image is an optimal image for the respective image type may be received as an output of the trained machine learning model. In some examples, the prediction output may include a predicted orientation of the probe resulting in the optimal or non-optimal image. Based on the prediction, at step 2210, instructions may be provided to the computing device (e.g., imaging computing device 136) to cause the computing device to perform an action associated with the medical image or prompt the operator to make probe adjustments.

For example, if the medical image is predicted as being an optimal image for the respective image type, the instructions provided to the computing device may be commands causing the computing device to automatically freeze the live medical image and capture (e.g., record and save) a still image. In other examples, rather than the computing device automatically performing these actions, the instructions may alternatively cause display of a prompt for the operator to perform these actions (e.g., using control elements on the application user interface to freeze and capture the still image). Once the still image of the respective image type is captured, steps 2204-2208 may be repeated for a next image type in the minimum set of image types to be obtained for the type of procedure received at step 2202. This may continue until still images for all image types in the minimum set of image types are obtained.

As another example, if the medical image is predicted as being a non-optimal image for the respective image type, the instructions provided to the computing device cause display of a prompt for the operator to make probe adjustments (e.g., reorient the probe) to allow capture of an optimal image for the respective image type. For example, the prompt may include directional instructions to guide the operator to adjust a current orientation of the probe corresponding to the predicted orientation in order to achieve an optimal image capture. For example, as part of the training, the trained machine learning model may learn a probe orientation associated with an optimal image for the respective image type from the labeled training medical images. Accordingly, the learned probe orientation associated with optimal image capture for the respective image type may be compared to the current probe orientation to generate directional instructions to adjust the current probe orientation to the learned probe orientation. In some examples, the directional instructions may be in the form of probe direction indicators similar to the probe direction indicators discussed above with reference to FIGS. 10 and 15. Steps 2204-2208 of the exemplary method 2200 may then be iteratively repeated as the probe is reoriented (e.g., is adjusted responsive to the directional instructions) until an optimal image for the respective image type is predicted and captured.

Figure 23:
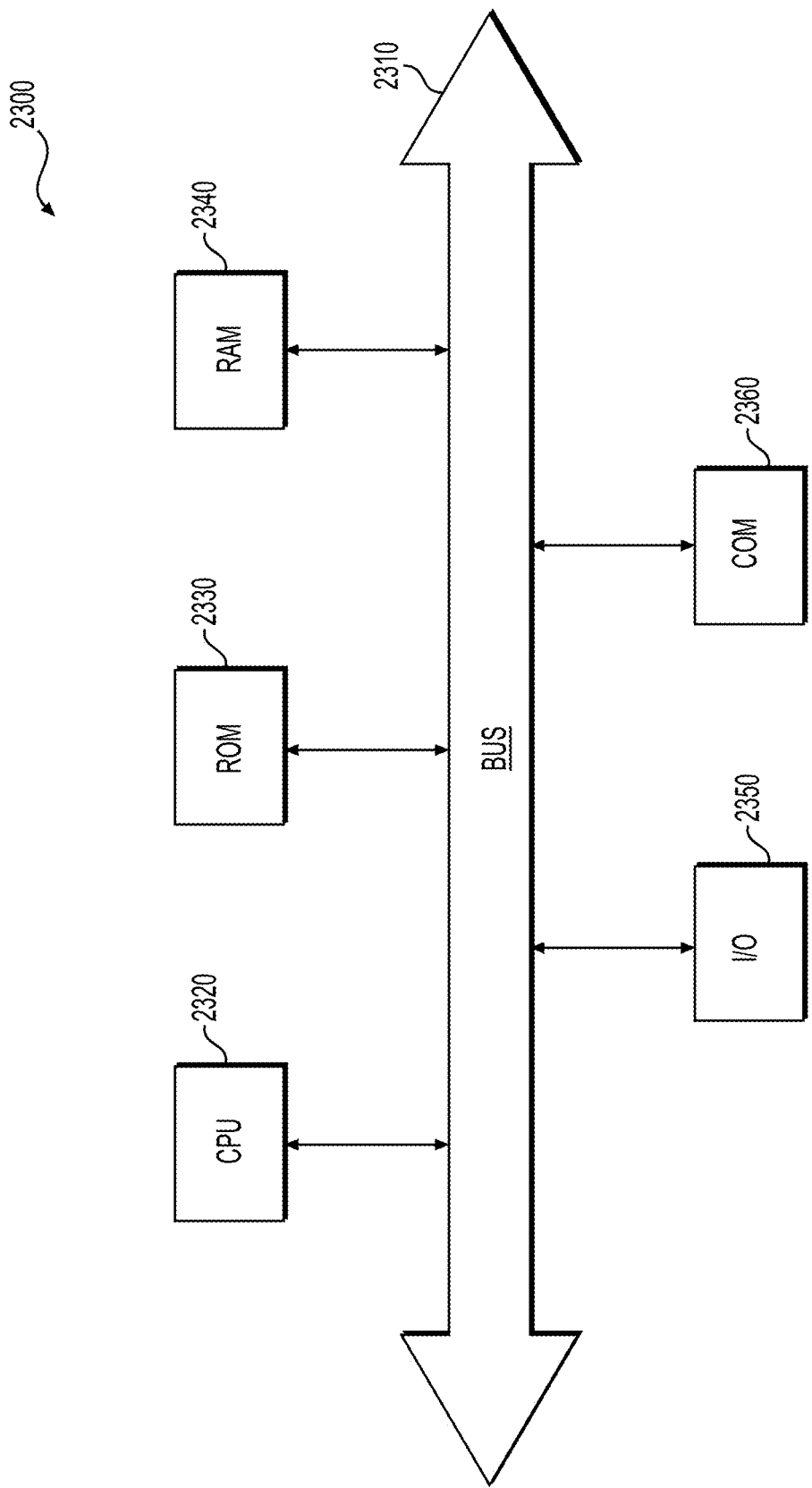
FIG. 23 illustrates an example system that may execute techniques presented herein.

FIG. 23 illustrates an example system or device 2300 that may execute techniques presented herein. Device 2300 may include a central processing unit (CPU) 2320. CPU 2320 may be any type of processor device including, for example, any type of special purpose or a general-purpose microprocessor device. As will be appreciated by persons skilled in the relevant art, CPU 2320 also may be a single processor in a multi-core/multiprocessor system, such as a system operating alone, or in a cluster of computing devices operating in a cluster or server farm. CPU 2320 may be connected to a data communication infrastructure 2310, for example a bus, message queue, network, or multi-core message-passing scheme.

Device 2300 may also include a main memory 2340, for example, random access memory (RAM), and also may include a secondary memory 2330. Secondary memory 2330, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 2330 may include similar means for allowing computer programs or other instructions to be loaded into device 2300. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 2300.

Device 2300 also may include a communications interface ("COM") 2360. Communications interface 2360 allows software and data to be transferred between device 2300 and external devices. Communications interface 2360 may include a modem, a network interface (such as an Ethernet card), a communications port, a PCMCIA slot and card, or the like. Software and data transferred via communications interface 2360 may be in the form of signals, which may be electronic, electromagnetic, optical or other signals capable of being received by communications interface 2360. These signals may be provided to communications interface 2360 via a communications path of device 2300, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 2300 may also include input and output ports 2350 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A system communicatively coupled to an ultrasound imaging system for processing musculoskeletal ultrasound images captured by the ultrasound imaging system, the system comprising:
    a processor; and
    a memory coupled to the processor and storing instructions that, when executed by the processor, cause the system to perform operations comprising:
        generating and providing, to the ultrasound imaging system, instructions to cause a first user interface of an application executing on the ultrasound imaging system to be displayed by the ultrasound imaging system, the first user interface including a plurality of objects of one or more object types, the one or more object types including anatomical features of an anatomical structure, atypical features present in the anatomical structure that are indicative of musculoskeletal conditions, and/or instruments inserted into the anatomical structure as part of a musculoskeletal procedure;
        receiving, from the ultrasound imaging system, an indication of a selection, via the displayed first user interface, of a particular object of interest, from the plurality of objects, to visually indicate within an ultrasound image of an anatomical structure of a musculoskeletal system to be captured and displayed by the ultrasound imaging system;
        receiving, from the ultrasound imaging system, the ultrasound image of the anatomical structure of the musculoskeletal system captured by the ultrasound imaging system;
        providing the ultrasound image as input to a machine learning model that is trained to identify the plurality of objects;
        receiving a prediction of a subset of two or more of the plurality of objects, including the particular object of interest, identified in the ultrasound image as output of the machine learning model; and
        based on the prediction and the received indication of the particular object of interest selected, generating and providing, to the ultrasound imaging system, instructions to cause a second user interface of the application to be displayed by the ultrasound imaging system, the second user interface including the ultrasound image with only the particular object of interest, of the subset, visually indicated in association with a location of the particular object of interest on the ultrasound image.

2. The system of claim 1, wherein the instructions include a corresponding object type, of the one or more object types, for the particular object of interest to cause a labeling of the particular object of interest with the corresponding object type in the second user interface.

3. The system of claim 1, the operations further comprising:
    determining measurements associated with the particular object of interest, wherein the second user interface further includes the measurements visually indicated in association with the location of the particular object of interest on the ultrasound image.

4. The system of claim 1, wherein the machine learning model is one of a plurality of machine learning models stored in one or more storage devices, and the operations further comprises:
    based on the particular object of interest selected, identifying and obtaining, from the plurality of machine learning models stored in the one or more storage devices, the machine learning model that is trained to identify at least the particular object of interest selected.

5. The system of claim 1, wherein the location of the particular object of interest is a first location, and the operations further comprise:
    receiving, from the ultrasound imaging system, an indication of a selection, via the displayed second user interface, to place a visual lock on the particular object of interest;
    in response to receiving, from the ultrasound imaging system, a new ultrasound image captured by the ultrasound imaging system, and based on the received indication of the selection to place the visual lock, determining a second location of the particular object of interest in the new ultrasound image; and
    generating and providing, to the ultrasound imaging system, instructions to cause a third user interface of the application to be displayed by the ultrasound imaging system, the third user interface including the new ultrasound image and the particular object of interest visually indicated in association with the second location of the particular object of interest on the new ultrasound image.

6. The system of claim 1, wherein the machine learning model is a first machine learning model, and the operations further comprising:
    providing the ultrasound image as input to a second machine learning model that is trained to identify whether the ultrasound image is an optimal image of the particular object of interest identified by the first machine learning model.

7. The system of claim 6, wherein the second machine learning model outputs a prediction that the ultrasound image is a non-optimal image, and the operations further comprising:
    predicting a current orientation of a probe of the ultrasound imaging system associated with the capture of the ultrasound image by the ultrasound imaging system;
    generating a prompt for an operator to adjust an orientation of the probe from the current orientation to a new orientation learned by the second machine learning model to capture an optimal image of the particular object of interest; and
    providing the prompt to the ultrasound imaging system for display.

8. The system of claim 1, wherein the machine learning model is a first machine learning model, the particular object of interest selected includes an instrument, from the instruments inserted into the anatomical structure as part of the musculoskeletal procedure, to reach a target, and the operations further comprising:
  receiving a sequence of ultrasound images, including the ultrasound image, captured by the ultrasound imaging system;
  providing the sequence of ultrasound images as input to a second machine learning model trained to predict instrument location; and
  receiving a predicted location of the instrument as output of the second machine learning model.

9. The system of claim 8, the operations further comprising:
  receiving a location of insertion of the instrument, wherein the location of insertion of the instrument is extracted from the sequence of ultrasound images or is received as operator input;
  determining an insertion angle of the instrument based on the location of insertion of the instrument and the predicted location of the instrument;
  providing the sequence of ultrasound images, the predicted location of the instrument, and the insertion angle of the instrument as input to a third machine learning model trained to predict trajectories of instruments;
  receiving a predicted trajectory of the instrument to reach the target as output of the third machine learning model;
  generating a three-dimensional representation of the anatomical structure based on the sequence of ultrasound images; and
  generating and providing, to the ultrasound imaging system, instructions to cause a third user interface of the application to be displayed by the ultrasound imaging system, the third user interface including the three-dimensional representation and the predicted trajectory visually indicated on the ultrasound image.

10. The system of claim 1, wherein the plurality of objects of the one or more object types include at least the anatomical features of the anatomical structure, and the anatomical features include bones, tendons, ligaments, cartilage, muscles, nerves, veins, or arteries.

11. The system of claim 10, wherein the plurality of objects of the one or more object types include at least the atypical features present in the anatomical structure that are indicative of musculoskeletal conditions, and the atypical features include ganglions, effusions, calcium deposits, masses, lesions, tears, restrictions, impingements, compressions, hemorrhages, edema, hematomas, fluid collections, inflammation, a defects, scars, fractures, avulsions, callus formations, infarctions, or foreign bodies.

12. The system of claim 11, wherein the plurality of objects of the one or more object types include at least the instruments inserted into the anatomical structure as part of the musculoskeletal procedure, and the instruments include needles, scalpels, knifes, tools, or balloons.

13. A method, performed by a system communicatively coupled to an ultrasound imaging system, for processing musculoskeletal ultrasound images captured by the ultrasound imaging system, the method comprising:
  generating and providing, to the ultrasound imaging system, instructions to cause a first user interface of an application executing on the ultrasound imaging system to be displayed by the ultrasound imaging system, the first user interface including a plurality of objects of one or more object types, the one or more object types including anatomical features of an anatomical structure, atypical features present in the anatomical structure that are indicative of musculoskeletal conditions, and/or instruments inserted into the anatomical structure as part of a musculoskeletal procedure;
  receiving, from the ultrasound imaging system, an indication of a selection, via the displayed first user interface, of a particular object of interest, from the plurality of objects, to visually indicate within an ultrasound image of an anatomical structure of a musculoskeletal system to be captured and displayed by the ultrasound imaging system;
  receiving, from the ultrasound imaging system, the ultrasound image of the anatomical structure of the musculoskeletal system captured by the ultrasound imaging system;
  providing the ultrasound image as input to a machine learning model that is trained to identify the plurality of objects;
  receiving a prediction of a subset of two or more of the plurality of objects, including the particular object of interest, identified in the ultrasound image as output of the machine learning model; and
  based on the prediction and the received indication of the particular object of interest selected, generating and providing, to the ultrasound imaging system, instructions to cause a second user interface of the application to be displayed by the ultrasound imaging system, the second user interface including the ultrasound image with only the particular object of interest, of the subset, visually indicated in association with a location of the particular object of interest on the ultrasound image.

14. The method of claim 13, wherein the instructions include a corresponding object type, of the one or more object types, for the particular object of interest to cause a labeling of the particular object of interest with the corresponding object type in the second user interface.

15. The method of claim 13, further comprising:
  determining measurements associated with the particular object of interest-, wherein the second user interface further includes the measurements visually indicated in association with the location of the particular object of interest on the ultrasound image.

16. The method of claim 13, wherein the machine learning model is a first machine learning model, and the method further comprising:
  providing the ultrasound image as input to a second machine learning model that is trained to identify whether the ultrasound image is an optimal image of the particular object of interest identified by the first machine learning model.

17. The method of claim 16, wherein the second machine learning model outputs a prediction that the ultrasound image is a non-optimal image, and the method further comprising:
  predicting a current orientation of a probe of the ultrasound imaging system associated with the capture of the ultrasound image by the ultrasound imaging system;
  generating a prompt for an operator to adjust an orientation of the probe from the current orientation to a new orientation learned by the second machine learning model to capture an optimal image of the particular object of interest identified; and
  providing the prompt to the ultrasound imaging system for display.

18. The method of claim 13, wherein the machine learning model is a first machine learning model, the particular object of interest selected includes an instrument, from the instruments inserted into the anatomical structure as part of the musculoskeletal procedure, to reach a target, and the method further comprising:

receiving a sequence of ultrasound images, including the ultrasound image, captured by the ultrasound imaging system;

providing the sequence of ultrasound images as input to a second machine learning model trained to predict instrument location; and receiving a predicted location of the instrument as output of the second machine learning model.

19. The method of claim 18, further comprising:

receiving a location of insertion of the instrument, wherein the location of insertion of the instrument is extracted from the sequence of ultrasound images or is received as operator input;

determining an insertion angle of the instrument based on the location of insertion of the instrument and the predicted location of the instrument;

providing the sequence of ultrasound images, the predicted location of the instrument, and the insertion angle of the instrument as input to a third machine learning model trained to predict trajectories of instruments to targets;

receiving a predicted trajectory of the instrument to reach the target as output of the third machine learning model;

generating a three-dimensional representation of the anatomical structure based on the sequence of ultrasound images; and generating and providing, to the ultrasound imaging system, instructions to cause a third user interface of the application to be displayed by the ultrasound imaging system, the third user interface including the three-dimensional representation and the predicted trajectory visually indicated on the ultrasound image.

20. A non-transitory computer-readable medium storing instructions that, when executed by a processor of a system communicatively coupled to an ultrasound imaging system, cause the processor to perform operations for processing musculoskeletal ultrasound images captured by the ultrasound imaging system, the operations comprising:

generating and providing, to the ultrasound imaging system, instructions to cause a first user interface of an application executing on the ultrasound imaging system to be displayed by the ultrasound imaging system, the first user interface including a plurality of objects of one or more object types, the one or more object types including anatomical features of an anatomical structure, atypical features present in the anatomical structure that are indicative of musculoskeletal conditions, and/or instruments inserted into the anatomical structure as part of a musculoskeletal procedure;

receiving, from the ultrasound imaging system, an indication of a selection, via the displayed first user interface, of a particular object of interest, from the plurality of objects, to visually indicate within an ultrasound image of an anatomical structure of a musculoskeletal system to be captured and displayed by the ultrasound imaging system;

receiving, from the ultrasound imaging system, the ultrasound image of the anatomical structure of the musculoskeletal system captured by the ultrasound imaging system;

providing the ultrasound image as input to a machine learning model that is trained to identify the plurality of objects;

receiving a prediction of a subset of two or more of the plurality of objects including the particular object of interest, identified in the ultrasound image as output of the machine learning model; and based on the prediction and the received indication of the particular object of interest selected, generating and providing, to the ultrasound imaging system instructions to cause a second user interface of the application to be displayed by the ultrasound imaging system, the second user interface including the ultrasound image with only the particular object of interest, of the subset, visually indicated in association with a location of the particular object of interest on the ultrasound image.

* * * * *